(12) United States Patent
Bruinsma et al.

(10) Patent No.: US 9,113,645 B2
(45) Date of Patent: Aug. 25, 2015

(54) SOLVENT EXTRACTION OF OIL FROM DISTILLERS DRIED GRAINS AND METHODS OF USING EXTRACTION PRODUCTS

(71) Applicant: Novita, LLC, Brookings, SD (US)

(72) Inventors: Keith Bruinsma, Brookings, SD (US); Donald Endres, Brookings, SD (US); Steven J. Furcich, Monticello, IL (US)

(73) Assignee: Novita Nutrition, LLC, Brookings, SD (US)

( * ) Notice: Subject to any disclaimer, the term of this patent is extended or adjusted under 35 U.S.C. 154(b) by 148 days.

(21) Appl. No.: 13/840,784

(22) Filed: Mar. 15, 2013

(65) Prior Publication Data

US 2013/0216688 A1    Aug. 22, 2013

Related U.S. Application Data

(63) Continuation-in-part of application No. 13/494,825, filed on Jun. 12, 2012, which is a continuation of application No. 12/442,934, filed as application No. PCT/US2007/079575 on Sep. 26, 2007, now Pat. No. 8,227,015.

(60) Provisional application No. 60/847,188, filed on Sep. 26, 2006.

(51) Int. Cl.
*A23J 1/12* (2006.01)
*A23K 1/06* (2006.01)
(Continued)

(52) U.S. Cl.
CPC ... *A23J 1/12* (2013.01); *A23K 1/06* (2013.01); *C10L 1/026* (2013.01); *C11B 1/10* (2013.01); *C11C 3/10* (2013.01); *C10L 1/08* (2013.01); *C10L 2290/544* (2013.01); *Y02E 50/13* (2013.01)

(58) Field of Classification Search
CPC .................................... A23J 1/12; A23K 1/06
See application file for complete search history.

(56) References Cited

U.S. PATENT DOCUMENTS

| | | | |
|---|---|---|---|
| 2,524,718 | A | 10/1950 | Stark et al. |
| 4,246,184 | A | 1/1981 | Pressick et al. |

(Continued)

FOREIGN PATENT DOCUMENTS

| | | |
|---|---|---|
| GB | 486163 | 5/1938 |
| WO | WO 2006/102685 A1 | 9/2006 |

(Continued)

OTHER PUBLICATIONS

Owsley,W.F., et al., Swine Diet Recommendations for Alabama, Alabama Cooperative Extension System, 1994, Agricultural & Natural Resources Animal Science, Circular ANR-639, pp. 1-12.*

(Continued)

*Primary Examiner* — Yate K Cutliff
(74) *Attorney, Agent, or Firm* — Patterson Thuente Pedersen, P.A.

(57) ABSTRACT

A process for extraction of crude oil from distillers dried grain solubles and/or distillers dried grains and producing corn distillers meal that may be used as a livestock supplement is disclosed. For example, the corn distillers meal may be used as a crude protein supplement for use in a livestock feed diet or a poultry feed diet. The solvent extracted crude oil may be suitable for oleochemical processing for personal care and home care products, biodiesel production, and/or renewable diesel production from hydro-treating the extracted oil to make green diesel fuel.

34 Claims, 5 Drawing Sheets

(51) Int. Cl.
*C11B 1/10* (2006.01)
*C10L 1/02* (2006.01)
*C11C 3/10* (2006.01)
*C10L 1/08* (2006.01)

(56) References Cited

U.S. PATENT DOCUMENTS

| | | | |
|---|---|---|---|
| 4,307,064 | A | 12/1981 | Barger et al. |
| 4,313,912 | A | 2/1982 | Barger |
| 4,332,092 | A | 6/1982 | Hansotte |
| 4,617,270 | A | 10/1986 | Anderson et al. |
| 5,260,089 | A * | 11/1993 | Thornberg ............ 426/624 |
| 5,591,416 | A | 1/1997 | Kemper et al. |
| 5,705,133 | A | 1/1998 | Kemper et al. |
| 5,992,050 | A | 11/1999 | Kemper et al. |
| 6,313,328 | B1 | 11/2001 | Ulrich et al. |
| 6,509,051 | B1 | 1/2003 | Wills |
| 6,732,454 | B2 | 5/2004 | Anderson et al. |
| 6,766,595 | B2 | 7/2004 | Anderson |
| 6,996,917 | B2 | 2/2006 | Anderson |
| 7,083,954 | B2 * | 8/2006 | Jakel et al. ............ 435/134 |
| 8,017,165 | B2 | 9/2011 | Kemper et al. |
| 8,080,274 | B2 | 12/2011 | Binder et al. |
| 8,227,015 | B2 | 7/2012 | Bruinsma et al. |
| 8,236,977 | B2 | 8/2012 | Woods et al. |
| 2004/0087808 | A1 | 5/2004 | Prevost et al. |
| 2006/0029715 | A1 | 2/2006 | Cheryan |
| 2006/0040024 | A1 | 2/2006 | Srinivasan et al. |
| 2007/0037993 | A1 | 2/2007 | Cheryan |
| 2009/0181153 | A1 | 7/2009 | Bendorf et al. |
| 2010/0092603 | A1 | 4/2010 | Bruinsma et al. |
| 2012/0294977 | A1 | 11/2012 | Bruinsma et al. |

FOREIGN PATENT DOCUMENTS

| | | |
|---|---|---|
| WO | WO 2008/039859 A2 | 4/2008 |
| WO | WO 2008/061190 A2 | 5/2008 |

OTHER PUBLICATIONS

Wondra K.J., et al., Effects of Particle Size and Pelleting on Growth Performance, Nutrient Digestibility, and Stomach Morphology in Finishing Pigs., 1995, Journal of Animal, Science, vol. 73, No. 3, pp. 757-763.*

AAFCO 2012 Official Publication—Model Regulations under the Model Bill, pp. 105-110 (2012).

Anderson et al., "Determination and prediction of digestible and metabolizable energy from chemical analysis of corn coproducts fed to finishing pigs", J. Anim. Sci., 2012, vol. 90, pp. 1242-1254.

Darling Investor and Analyst Forum presentation (Sep. 12, 2012), 104 pages.

Jacela et al., "Amino acid digestibility and energy content of deoiled (solvent-extracted) corn distillers dried grains with soluble for swine and effects on growth performance and carcass characteristics", J. Anim. Sci., 2011, vol. 89, pp. 1817-1829.

Loosli et al., "Comparative Value of Corn Distillers Dried Grains with Solubles, Soybean Oil Meal, and Linseed Oil Meal for Milk Production", Journal of Dairy Science, 1960, vol. 43, No. 6, pp. 816-820.

Lumpkins et al., "Evaluation of Distillers Dried Grains with Solubles as a Feed Ingredient for Broilers", Poultry Science, 2004, vol. 83, pp. 1891-1896.

Mjoun et al., "Lactation performance and amino acid utilization of cows fed increasing amounts of reduced-fat dried distillers grains with soluble", J. Dairy Sci., 2010, vol. 93, No. 1, pp. 288-303.

Mjoun et al, "Performance and amino acid utilization of early lactation dairy cows fed regular or reduced-fat dried distillers grains with solubles", J. Dairy Sci., 2010, vol. 93, No. 7, pp. 3176-3191.

Mjoun et al., "Ruminal degradability and intestinal digestibility of protein and amino acids in soybean and corn distillers grains products", J. Dairy Sci., 2010, vol. 93, No. 9, pp. 4144-4154.

Singh et al., "Technical Note: Extraction of Oil from Corn Distillers Dried Grains with Solubles", Transactions of the ASAE, copyright 1998, vol. 41, No. 6, pp. 1775-1777.

Moreau et al, Chapter 15 "Corn Kernel Oil and Corn Fiber Oil", Reprinted from Gourmet and Health-Promoting Specialty Oils, copyright 2009, pp. 409-431.

Nalco—Corn Oil Extraction Optimization presentation, 2011, 15 pages.

Nalco—Corn Oil Extraction Optimization presentation, prior to Mar. 14, 2013, 21 pages.

Dr. Jerry Shurson, University of Minnesota, "DDGS: An Evolving Commodity" Presentation, (prior to Jan. 16, 2013), 31 pages.

Zhang et al., "The Occurrence and Concentration of Mycotoxins in U.S. Distillers Dried Grains with Solubles", J. Agric. Food Chem., 2009, vol. 57, pp. 9828-9837.

Zhang et al., "Survey of Mycotoxins in U.S. Distiller's Dried Grains with Solubles from 2009 to 2011", J. Agric. Food Chem., 2012, vol. 60, pp. 539-543.

Henry et al., "Animal & Veterinary Mycotoxins in Feeds: CVM's Perspective" Presentation, Aug. 23, 2006, 8 pages.

Oleochemical Roadmaps (3 images) (prior to Feb. 11, 2013).

* cited by examiner

SOLVENT EXTRACTION OF OIL FROM DISTILLERS DRIED GRAINS AND METHODS OF USING EXTRACTION PRODUCTS

RELATED APPLICATIONS

This patent application is a continuation-in-part of U.S. patent application Ser. No. 13/494,825, filed Jun. 12, 2012, which is a continuation of U.S. Pat. No. 8,227,015, filed Mar. 25, 2009, which is a National Stage Filing under 35 U.S.C. 37 of International Application No. PCT/US2007/079575, filed on Sep. 26, 2007, which designated the United States and which claims the benefit of U.S. Provisional Patent Application No. 60/847,188, filed Sep. 26, 2006, the contents of the foregoing priority U.S. and international patent applications and patents incorporated by reference in their entirety in the present patent application.

FIELD OF THE INVENTION

The present invention relates generally to the extraction of oil from distillers dried grains with solubles (DDGS) and/or distillers dried grains (DDG) to produce distillers meal, methods of using the oil extracted from DDGS and/or DDG, and methods of using the distillers meal. More particularly, described herein are methods for solvent extraction of crude oil from DDGS and/or DDG to provide distillers meal having a desired nutrient content, animal feed supplements containing distillers meal, methods of processing the extracted oil to provide oil suitable for consumer use, biodiesel production, renewable diesel production from hydro-treating the extracted oil to make green diesel fuel, and/or oleochemical production.

BACKGROUND OF THE INVENTION

Ethanol can be produced using grains, such as corn, which are renewable resources. Presently, the majority of ethanol-producing biorefineries in the United States are dry-grind corn biorefineries, and it is estimated that the present ethanol production capacity of such biorefineries runs into the billions of gallons each year. Co-products of the ethanol biorefining process are distillers dried grains and distillers dried grains with solubles. Based on current production rates of ethanol from dry-grind ethanol plants, approximately 40 million tons of DDGS are produced in the United States annually.

Over the past few decades, achieving an ethanol product from grain-based biorefineries that is both commercial viable and truly renewable has proven challenging. Two of the more significant hurdles are: 1) the cost of grain-based ethanol production; and 2) the energy input to output ratio of grain-based ethanol production processes. As is easily appreciated, these two problems are intertwined. Grain-based ethanol production has historically required significant and costly input of fossil fuels (e.g., natural gas) to drive the biorefining process. Moreover, the amount of fossil fuel that has been historically required to drive grain-based ethanol production is costly, particularly so as the cost of natural gas and other fossil fuels increases.

One of the ways by which the effective cost of grain-based ethanol production can be reduced is the sale of commercially valuable co-products of the biorefining process. DDGS are co-products of grain-based ethanol production processes that have recognized commercial value. In particular, DDGS are sold as a livestock feed supplement. Because it is primarily the starch of the grain that is consumed in the production of ethanol, the DDGS remaining after fermentation and distillation contain nutritionally valuable fiber, protein and fat. Relative to raw grain, DDGS may even be considered a superior feed, as they contain concentrated amounts of fiber, protein and fat, together with a significantly reduced amount of starch. In addition, DDGS are considerably less expensive than some feeds of comparable nutritional value.

DETAILED DESCRIPTION OF THE DRAWINGS

Figure 1:
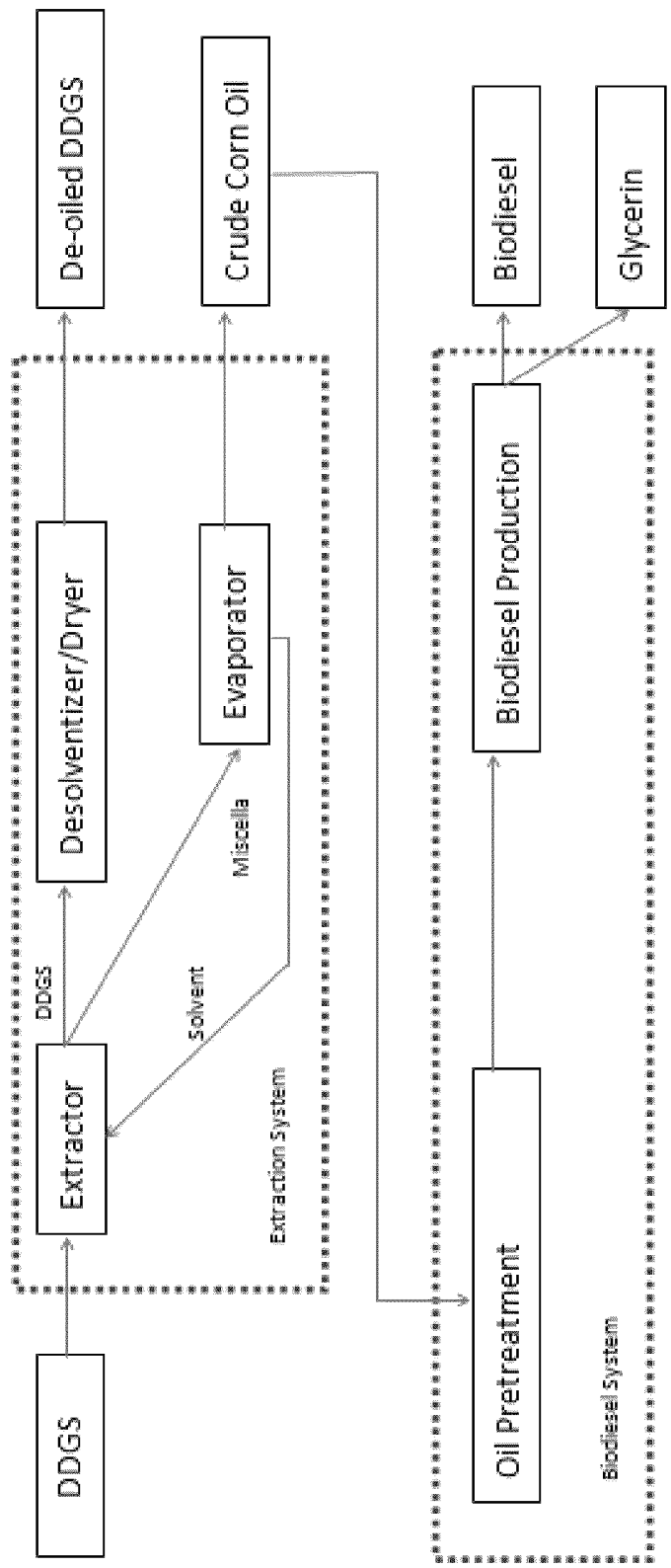
FIG. 1 provides a flow-chart representation of the process by which crude oil is extracted from DDGS and refined into biodiesel and glycerine.

It will be readily understood that the methods and materials as they are generally described and illustrated in the figures herein could be arranged and designed in a wide variety of different configurations. Thus, the following more detailed description of various embodiments of the methods and materials provided herein is not intended to limit the scope of the claims, but merely provides representative examples of various embodiments of the subject matter recited in the appended claims. For example, though DDGS are referenced herein with respect to the methods and materials described, it is to be understood that distillers dried grains (DDG) could also be utilized instead of or in addition to the DDGS. In particular, DDG retain significant oil content, and in embodiments of the processes and methods described herein DDG may be used in place of DDGS or in combination with DDGS. Moreover, DDG retain valuable nutrient properties and distillers meal, resulting from solvent extraction of DDG according to the methods described herein, may also be utilized as an animal feed supplement. Also, while every ethanol plant is configured differently, each ethanol plants handles recycle streams differently, including recycling different process streams of solubles to the distilled dried grains. Thus, the following description, while specific to DDGS, should also be understood to be applicable to DDG.

As is described herein, the commercial value of DDG and DDGS from grain-based ethanol production processes can be further enhanced. In particular, commercially valuable amounts of oil can be extracted from the DDG and DDGS using a solvent extraction process. The solvent extracted oil can then be further processed to provide, for example, food grade oil, such as food grade corn oil where the DDG and DDGS are derived from an ethanol biorefinery that utilizes corn grain as biomass. Alternatively, the oil extracted from DDG and DDGS can be subjected to a transesterification process, sometimes in conjunction with an esterification process, to yield biodiesel and glycerine. Alternatively, the oil extracted from DDG and DDGS can be subjected to a hydro-treating process to yield a renewable green diesel fuel.

Still alternatively, the oil extracted from DDG and DDGS can be subjected to other oleochemical processing, such as fat splitting (or hydrolysis) of the glycerides (e.g., triglyceride, diglyceride and monoglyceride) into different oleochemical fractions to produce crude fatty acids and glycerine. After the splitting process, the crude fatty acids may be subjected to additional processing, such as distillation, fractionation, and other methods of separation to produce crude, distilled and fractionated fatty acids. Likewise, the crude glycerine may be subjected to additional processing, such as adsorptive filtration using adsorptive materials, such as activated carbon, and distillation to produce refined glycerine. The fatty acids and/or glycerine may be subjected to further chemical and enzymatic reactions to yield desired oleochemicals for personal care products and home care products.

In some aspects, the glycerine is subjected to esterification and distillation processing to yield distilled esters of glycerol.

In some aspects, the crude fatty acids are subjected to esterification reactions to yield fatty acid esters or fatty acid methyl esters, esterification and distillation processing to yield distilled fractionated fatty esters, and/or esterification and epoxidation processing to yield alkyl epoxy esters. In some aspects, the crude fatty acids are subjected to ethoxylation processing to yield fatty acid ethoxylates. In some aspects, the crude fatty acids are subjected to conjugation processing to yield conjugated fatty acids. In some aspects, the crude fatty acids are subjected to hardening processing to yield saturated fatty acids. In some aspects, the crude fatty acids are subjected to hardening processing and then hydrogenation processing to yield fatty alcohols.

In some aspects, the crude fatty acids are subjected to esterification processing to yield fatty acid methyl esters or the extracted oil can undergo transesterification to yield fatty acid methyl esters. The fatty acid methyl esters may be subjected to hydrogenation to yield fatty alcohols, sulfonation processing to yield α-sulfo fatty acid esters, and/or amidation to yield fatty acid alkanolamides. In some aspects, the fatty alcohols derived from fatty acids or fatty acid methyl esters may then be subjected to Guerbet reaction to yield Guerbet alcohols, chlorination to yield alkyl chlorides, ethoxylation to yield fatty alcohol ethoxylates, sulfation to yield fatty alcohol sulfates and/or esterification to yield esters. The fatty alcohol ethoxylates may further under propoxylation to yield fatty alcohol alkoxylates, sulfation to yield fatty alcohol ether sulfates, phosphatization to yield fatty alcohol ether phosphates and/or sulfitation to yield fatty alcohol sulfosuccinates. In some aspects, the crude fatty acids are subjected to fractionation processing to yield C12, C14, C16 and/or C18 fractionated fatty acids.

The distillers meal resulting from solvent extraction as described herein is still suitable for use as an animal feed ingredient, such as, for example, a feed supplement or constituent for domestic pets, livestock (such as beef cattle, dairy cattle, equine, sheep and/or swine), aquaculture or poultry, including chickens, geese and/or turkey. Therefore, solvent extraction of DDG and DDGS according to the methods described herein may facilitate a reduction in the effective costs of producing ethanol from a grain-based biorefinery, as it allows for production of multiple, commercially-valuable products from DDG and DDGS.

In one embodiment, ethanol production, solvent extraction of DDGS, and refining of the crude oil removed from the DDGS can occur in a single facility. For example, in such an embodiment, a grain-based ethanol biorefinery may further include facilities for solvent extraction of the DDGS produced at the biorefinery. In another such embodiment, a grain-based ethanol biorefinery may further include facilities for solvent extraction of the DDGS produced at the biorefinery and facilities for processing the crude oil extracted from the DDGS to provide food-grade oil suitable for consumer use. In yet another embodiment, a grain-based ethanol biorefinery may further include facilities for solvent extraction of the DDGS produced at the biorefinery and facilities for processing and refining the crude oil extracted from the DDGS to produce biodiesel and glycerin. By integrating these operations within a single facility, process efficiencies may be gained and costs of solvent extracting the DDGS and processing or refining the extracted oil may be reduced.

Solvent Extraction of Crude Oil from DDGS and/or DDG

Using solvent extraction processes, commercially significant amounts of crude plant oils can be isolated from DDGS, while maintaining the value of DDGS as a feed supplement. In one embodiment, the DDGS used in a solvent extraction process as described herein are selected from DDGS generated in ethanol production processes that utilize corn, barley, rye, sorghum, or soybean grain. In another embodiment, the DDGS used in a solvent extraction process are corn DDGS generated from a dry-grind corn ethanol biorefinery.

Solvent extraction processes suitable for extraction of crude oil from DDGS include processes that utilize ethanol, hexane, iso-hexane, petroleum distillate, mixtures thereof, or one or more other suitable solvents, as known in the art, for oil extraction of DDGS. One of ordinary skill in the art will appreciate that such solvents may be commercial grade or reagent grade solvents. In some aspects, solvent extraction processes suitable for extraction of crude oil from DDGS or crude corn oil form corn DDGS include processes that utilize suitable non-polar solvents that have a high solvent power for lipids, are commercially available, are acceptable regulatory-recognized solvents and/or can be readily removed from the resulting product by commonly accepted methods such as distillation, washing and/or evaporation.

In some aspects, suitable non-polar solvents comprise saturated hydrocarbons, such as one or more $C_5$-$C_7$-alkanes, particularly n-pentane, n-hexane and n-heptane, as well as the structural isomers thereof (i.e., isopentane, neopentane, isohexane, 2-methylepentane, 2,3-dimethylbutane, neohexane, isoheptane, 2-methylhexane, 2,2-dimethylpentane, 2,3-dimethylpentane, 2,4-dimethylpentane, 3-ethylpentane, and 2,2,3-trimethylbutane), petroleum ether, or mixtures thereof. In some aspects, suitable non-polar solvents or mixtures thereof have a boiling point in the range from about 36° C. to about 99° C. In some aspects, the non-polar solvents may be purified or commercial grade. For example, in some aspects, a suitable non-polar solvent includes commercial grade hexane, which one of ordinary skill in the art will appreciate comprises a mixture of n-hexane, other isomers of hexane and small amounts of other miscellaneous hydrocarbons (i.e., acetone, methyl ethyl ketone, dichloromethane, and trichloroethylene, aromatics such as toluene and/or other types of petroleum hydrocarbons).

In some aspects, suitable solvents comprise mixtures of solvents containing alkanes or blends of polar and non-polar solvents that form azeotropes. For example, suitable blends of polar and non-polar solvents may include hexane:ethanol or hexane:isopropanol. Such solvents may also include ketones such as acetone. In some aspects, the azeotrope comprises a blend of polar and non-polar solvents, such that the blend is a positive azeotrope, which has a boiling point at a lower temperature than any other ratio of its constituents.

In one embodiment, the solvent extraction process utilizes a solvent, such as, for example, hexane that serves to remove oil from the DDGS without substantially altering the protein or fiber content of the DDGS. Oil extraction of the DDGS as described herein yields a distillers meal. In one embodiment, the solvent extraction process removes about 60% or more, about 65% or more, about 70% or more, about 75% or more, about 80% or more, or about 90% or more of the oil present in the DDGS. In another embodiment, the solvent extraction process is a hexane extraction process that removes about 60% or more, about 65% or more, about 70% or more, about 75% or more, about 80% or more, or about 90% or more of the oil present in the DDGS. In yet another embodiment, the solvent extraction process is a hexane extraction process that removes about 75% or more, about 80% or more, or about 90% or more of the oil present in corn DDGS. In yet another embodiment, the solvent extraction process is an extraction process using a mixture of non-polar solvents having a boiling point range between about 36° C. to about 99° C. that removes about 60% or more, about 65% or more, about 70% or more, about 75% or more, about 80% or more, or about 90% or more of the oil present in DDGS, and in some aspects corn DDGS. In yet another embodiment, the solvent extraction process is an extraction process using an azeotrope of a polar solvent and an alkane solvent that removes about 75% or more, about 80% or more, or about 90% or more of the oil present in DDGS, and in some aspects corn DDGS. In yet another embodiment, the solvent extraction process is a hexane extraction process that removes about 60% or more, about 65% or more, about 70% or more, about 75% or more, about 80% or more, or about 90% or more of the oil present in DDGS produced at a dry-grind corn ethanol biorefinery. Corn DDGS typically include about 5% up to about 15% by weight oil content, and in one embodiment, the solvent extraction process is a hexane extraction process that results in a corn distillers meal having a residual oil content of approximately 2-3% by weight, in some other aspects approximately 0.25-5% by weight, in some other aspects approximately 1-4% by weight, and in still some other aspects approximately 0.25-3% by weight. In another embodiment, corn DDGS are subjected to a hexane extraction process that results in a corn distillers meal having a residual oil content of no more than 3.0% by weight, in some aspects no more than 2.5% by weight.

Where the DDGS are produced at a dry-grind corn ethanol biorefinery, a flow-chart representation of suitable hexane extraction process is shown in FIG. 1. In a typical dry-grind process for ethanol production from corn, the DDGS are a co-product derived from the corn mash after the starch has been converted to ethanol and the ethanol has been removed by distillation. The stillage is typically subjected to centrifugation, evaporation and drying to remove residual liquid content, resulting in DDGS. Methods of extracting crude corn oil from corn DDGS are discussed in Sing et. al., "Extraction of Oil From Corn Distillers Dried Grains with Solubles", Transactions of the ASAE 41 (6), 1775-1777 (1998), the teachings of which are incorporated by reference herein. In addition, solvent extraction technologies and equipment are available from, for example, Crown Iron Works Company of Minneapolis, Minn., U.S.A. Moreover, technology directed to removal of the oil from vegetable particles, removal of residual solvent from solvent extracted materials, and recovery of solvents used in solvent extraction processes are described in, for example, U.S. Pat. No. 6,996,917, U.S. Pat. No. 6,766,595, U.S. Pat. No. 6,732,454, and U.S. Pat. No. 6,509,051. These patents are assigned to Crown Iron Works Company, and the teachings of each of these patents are incorporated by reference herein.

Referring again to FIG. 1, which illustrates an embodiment of a solvent extraction process that may be applied to DDGS, as a first step, DDGS meal is fed into an extractor. In some aspects, the DDGS meal may optionally be ground before being fed into an extractor to reduce the particle size of the DDGS meal. In some aspects, the DDGS meal is ground such that about 80%, in some aspects about 85%, in some aspects about 90%, in some aspects about 95%, in some aspects about 99%, and in some aspects about 100% of the DDGS meal has a particle size less than about 1 millimeter. In some aspects about 90% of the ground DDGS meal has a particle size less than about 1 millimeter to about 150 microns, in some aspects less than about 840 microns to about 150 microns, in some aspects less than about 710 microns to about 150 microns, in some aspects less than about 595 microns to about 150 microns, and in some other aspects less than about 525 microns to about 150 microns. In other aspects, the DDGS meal is ground such that at least 95% of the DDGS meal has a particle size less than about 1 millimeter to about 150 microns, in some aspects less than about 840 microns to about 150 microns, in some aspects less than about 710 microns to about 150 microns, in some aspects less than about 595 microns to about 150 microns, and in some other aspects less than about 525 microns to about 150 microns. In some other aspects, the DDGS meal is ground such that about 99% of the DDGS meal has a particle size less than about 1 millimeter to about 150 microns, in some aspects less than about 840 microns to about 150 microns, in some aspects less than about 710 microns to about 150 microns, in some aspects less than about 595 microns to about 150 microns, and in some other aspects less than about 525 microns to about 150 microns.

In the extractor, the DDGS meal is washed with solvent, and in one embodiment, the DDGS meal is turned at least once in order to ensure that all DDGS particles are contacted as equally as practicable with solvent. After washing, the resulting mixture of oil and solvent, called miscella, is collected for separation of the extracted oil from the solvent. During the extraction process, as the solvent washes over the DDGS flakes, the solvent not only brings oil into solution, but may collect fine, solid DDGS particles. These "fines" are generally undesirable impurities in the miscella, and in one embodiment, the miscella is discharged from the separator through a device that separates or scrubs the fines from the miscella as the miscella is collected for separation of the oil from the solvent.

In order to separate the oil and the solvent contained in the miscella, the miscella may be subjected to a distillation step. In this step, the miscella can, for example, be processed through an evaporator, which heats the miscella to a temperature that is high enough to cause vaporization of the solvent, but is not sufficiently high to adversely affect or vaporize the extracted oil. The oil may be further stripped of solvent in an oil stripper to further reduce residual solvent levels. As the solvent evaporates, it may be collected, for example, in a condenser, and recycled for future use. Separation of the solvent from the miscella results in a stock of crude oil, which may be further processed to provide, for example, food grade oil for ultimately consumer uses or an oil product suitable for use in a renewable diesel process by hydro-treating the oil to produce green diesel or a transesterification process that yields fatty acid methyl esters for use in biodiesel and/or for ultimate use in the production of oleochemicals, as well as glycerine which may be produced as a consequent of processing the oil.

After extraction of the oil, the wet, de-oiled DDGS may be conveyed out of the extractor and subjected to a drying process that removes residual solvent. Removal of residual solvent is important to production of distillers meal suitable for use as an animal feed ingredient. In one embodiment, the wet meal can be conveyed in a vapor tight environment to preserve and collect solvent that transiently evaporates from the wet meal as it is conveyed into the desolventizer. As the meal enters the desolventizer, it may be heated to vaporize and remove the residual solvent. In order to heat the meal, the desolventizer may include a mechanism for distributing the meal over one or more trays, and the meal may be heated directly, such as through direct contact with heated air or steam, or indirectly, such as by heating the tray carrying the meal, or both. The desolventizer may further include multiple different trays for carrying the meal through different processing steps within the desolventizer. In order to facilitate transfer of the meal from one tray to another, the trays carrying the meal may include openings between trays that allow the meal to pass from one tray to the next.

Where the desolventizer utilizes multiple process steps to remove residual solvent from the wet, de-oiled DDGS to produce distillers meal, the wet, de-oiled DDGS may be loaded and transferred through various trays to facilitate heating and solvent removal in multiple process steps. For example, in one embodiment, as the meal enters the desolventizer, it may be loaded on a first group of heated trays where the meal is evenly distributed and solvent vapor is flashed from the meal. From this first set of trays, the meal may be transferred onto a second group of trays, where it is again evenly distributed. The second set of trays may be heated indirectly by steam. The trays may be designed to allow venting of the solvent from one tray to the next and the meal contained in the second set of trays travels counter current to the solvent vapors. A third tray or set of trays may be provided to allow direct steam injection into the meal, which works to strip remaining solvent. Where the desolventizer includes multiple trays and utilizes multiple desolventizing processes, the quantity of trays and their positions may be designed to allow maximum contact between vapors and meal.

From the desolventizer, the meal may be conveyed to a dryer where the meal is dried of residual excess water and cooled to provide a finished distillers meal. As it is conveyed into the dryer, the meal may be deposited into drying trays and it is warmed by heated air. As the meal is heated, residual water is vaporized. After drying, the meal may be cooled using ambient air. The desolventized, dried and cooled distillers meal may be stored, further processed, such as pelletizing to increase densification, or prepared for sale or distribution.

In some aspects, at least about 80%, in some aspects about 85%, in some aspects about 90%, in some aspects about 95%, in some aspects about 99%, and in some aspects about 100% of the distillers meal has a particle size less than about 1 millimeter. In some aspects about 90% of the distillers meal has a particle size less than about 1 millimeter to about 150 microns, in some aspects less than about 840 microns to about 150 microns, in some aspects less than about 710 microns to about 150 microns, in some aspects less than about 595 microns to about 150 microns, and in some other aspects less than about 525 microns to about 150 microns. In other aspects, about 95% of the distillers meal has a particle size less than about 1 millimeter to about 150 microns, in some aspects less than about 840 microns to about 150 microns, in some aspects less than about 710 microns to about 150 microns, in some aspects less than about 595 microns to about 150 microns, and in some other aspects less than about 525 microns to about 150 microns. In some other aspects, about 99% of the distillers meal has a particle size less than about 1 millimeter to about 150 microns, in some aspects less than about 840 microns to about 150 microns, in some aspects less than about 710 microns to about 150 microns, in some aspects less than about 595 microns to about 150 microns, and in some other aspects less than about 525 microns to about 150 microns.

In some aspects, the distillers meal has an average particle size of about 105 microns to about 625 microns, in some aspects about 150 microns to about 600 microns, in some aspects about 175 microns to about 575 microns, in some aspects about 200 microns to about 525 microns, and in some aspects about 250 microns to about 500 microns.

In some aspects, the distillers meal may comprise a residual level of solvent utilized in the solvent extraction process in an amount of about 10 ppm to about 2000 ppm, in other aspects about 10 ppm to about 1000 ppm, in other aspects about 10 ppm to about 500 ppm, and still in some other aspects about 10 ppm to about 100 ppm. In some aspects, a residual level of hexane solvent is present in the distillers meal in an amount of about 10 ppm to about 2000 ppm, in other aspects about 10 ppm to about 1000 ppm, in other aspects about 10 ppm to about 500 ppm, in other aspects about 10 ppm to about 100 ppm, and in still other aspects about 100 ppm to about 500 ppm. In some aspects, a residual level of hexane solvent is present in the corn distillers meal in an amount of about 10 ppm to about 2000 ppm, in other aspects about 10 ppm to about 1000 ppm, in other aspects about 10 ppm to about 500 ppm, in other aspects about 10 ppm to about 100 ppm, and in still other aspects about 100 ppm to about 500 ppm.

In some aspects, the distillers meal may comprise a residual moisture content of about 3% to about 15%, in some aspects about 4% to about 13%, and still in other aspects about 7% to about 11%.

The biorefining and solvent extraction processes may be tailored to provide extracted oil exhibiting specific qualities. For example, where the DDGS are corn DDGS and the solvent extraction process is a hexane extraction process, the biorefining and solvent extraction process may be controlled to provide an extracted crude corn oil exhibiting no more than about 15% by weight free fatty acids, such as oleic acid, no more than about 1% by weight crude protein, about 0.5% by weight total nitrogen, 0.2% by weight ash, about 0.05% phosphorus, about 0.01% by weight potassium, about 0.005% sodium, or about 0.05% by weight sulfur, or any combination of one or more such qualities. In one such embodiment, the crude corn oil includes no more than about 0.6%, 0.7%, 0.8% or 0.9% by weight crude protein. In another such embodiment, the crude corn oil contains no more than about 10%, 11%, 12%, 13%, 14%, or 15% by weight free fatty acids. In another such embodiment, the crude corn oil contains free fatty acids in an amount between about 1% to about 15%, in some aspects between about 1% and about 14%, in some aspects between about 1% and about 13%, in some aspects between about 1% and about 12%, in some aspects between about 1% and about 11%, in some aspects between about 1% and about 10%, in some aspects between about 1% and about 9%, in some aspects about 1% and about 8%, in some aspects about 3% to about 15%, by weight of the crude corn oil, with other ranges and subranges of the foregoing ranges contemplated. In another such embodiment, the crude corn oil contains no more than about 0.09%, 0.1%, 0.2%, 0.25%, 0.3%, or 0.4% by weight total nitrogen. In yet another such embodiment, the crude corn oil contains no more than about 0.08%, 0.09%, 0.1%, or 0.15% by weight ash. In another such embodiment, the crude corn oil contains no more than about 0.02%, 0.03%, or 0.04% by weight phosphorus. In yet another such embodiment, the crude corn oil contains no more than about 0.02%, 0.03%, or 0.04% by weight potassium. In yet another such embodiment, the crude corn oil contains no more than about 0.003% or 0.004% by weight sodium. In yet another such embodiment, the crude corn oil contains no more than about 0.02%, 0.03%, or 0.04% by weight sulfur.

It is contemplated that where the DDGS is corn DDGS and the solvent extraction process utilizes other solvents or mixtures of solvents containing alkanes, the biorefining and solvent extraction process may be controlled to provide an extracted crude oil exhibiting no more than about 15% by weight free fatty acids, such as oleic acid, no more than about 1% by weight crude protein, 0.5% by weight total nitrogen, 0.2% by weight ash, 0.05% phosphorus, 0.01% by weight potassium, 0.005% sodium, or 0.05% by weight sulfur, or any combination of one or more such qualities. In one such embodiment, the crude corn oil includes no more than about 0.6%, 0.7%, 0.8% or 0.9% by weight crude protein. In another such embodiment, the crude oil contains no more than about 10%, 11%, 12%, 13%, 14%, or 15% by weight free fatty acids. In another such embodiment, the crude corn oil contains free fatty acids in an amount between about 1% to about 15%, in some aspects between about 1% and about 14%, in some aspects between about 1% and about 13%, in some aspects between about 1% and about 12%, in some aspects between about 1% and about 11%, in some aspects between about 1% and about 10%, in some aspects between about 1% and about 9%, in some aspects about 1% and about 8%, in some aspects about 3% to about 15%, by weight of the crude corn oil, with other ranges and subranges of the foregoing ranges contemplated. In another such embodiment, the crude corn oil contains no more than about 0.09%, 0.1%, 0.2%, 0.25%, 0.3%, or 0.4% by weight total nitrogen. In yet another such embodiment, the crude corn oil contains no more than about 0.08%, 0.09%, 0.1%, or 0.15% by weight ash. In another such embodiment, the crude corn oil contains no more than about 0.02%, 0.03%, or 0.04% by weight phosphorus. In yet another such embodiment, the crude corn oil contains no more than about 0.01%, 0.02%, 0.03%, or 0.04% by weight potassium. In yet another such embodiment, the crude corn oil contains no more than about 0.003% or 0.004% by weight sodium. In yet another such embodiment, the crude corn oil contains no more than about 0.02%, 0.03%, or 0.04% by weight sulfur.

In some aspects, the crude oil extracted utilizing a solvent extraction process on DDGS comprises a residual level of solvent utilized in the solvent extraction process in an amount of about 1 ppm to about 500 ppm, in other aspects about 10 ppm to about 400 ppm, in other aspects about 1 ppm to about 100 ppm, and still in some other aspects about 10 ppm to about 100 ppm. In some aspects, a residual level of solvent is present in the crude corn oil extracted from corn DDGS, the residual level of hexane present in the crude oil present in an amount of about 1 ppm to about 500 ppm, in other aspects about 10 ppm to about 400 ppm, in other aspects about 1 ppm to about 100 ppm, and still in some other aspects about 10 ppm to about 100 ppm. In some aspects, a residual level of hexane solvent is present in the crude oil extracted from DDGS, the residual level of hexane present in the crude oil present in an amount of about 1 ppm to about 500 ppm, in other aspects about 10 ppm to about 400 ppm, in other aspects about 1 ppm to about 100 ppm, and still in some other aspects about 10 ppm to about 100 ppm. In some aspects, a residual level of hexane solvent is present in the crude corn oil extracted from corn DDGS, the residual level of hexane present in the crude oil present in an amount of about 1 ppm to about 500 ppm, in other aspects about 10 ppm to about 400 ppm, in other aspects about 1 ppm to about 100 ppm, and still in some other aspects about 10 ppm to about 100 ppm.

In comparing the contents of corn stillage oil (CSO), which is corn oil extracted from the stillage of an ethanol process, to that of crude corn oil extracted utilizing a solvent extraction process on corn DDGS, the content of phosphorous and phosphorous containing compounds in CSO is more than about 100 ppm, and in some instances more than about 105 ppm, which is higher than solvent extracted crude corn oil, which in some aspects can have phosphorous and phosphorous containing compounds in an amount of about 1 ppm to about 50 ppm. Without wishing to be bound by theory, while corn contains some native phosphorus content, which is primarily in the form of phospholipids or phosphatides, the majority of phosphorous is contributed by chemical addition during the ethanol process. The chemical forms of phosphorous, including phosphates, have a relatively high degree of solubility in water. Thus, in the process of recovering CSO, it is expected the various phosphorous forms would be partially washed out with the CSO, and some residual phosphorous content would remain in the CSO. Conversely, these same water soluble phosphorous compounds are not easily extracted with non-polar solvents, such as hexane. Consequently, crude corn oil extracted by a solvent extraction process from corn DDGS contain initial levels of phosphorous and phosphorous containing compounds in an amount of about 1 ppm to about 50 ppm, in some other aspects about 1 ppm to about 20 ppm, in some other aspects about 1 ppm to about 10 ppm, and in still other aspects about 1 ppm to about 5 ppm.

In comparing the contents of CSO to that of crude corn oil extracted utilizing a solvent extraction process on corn DDGS, the content of sulfur and sulfur containing compounds in CSO is more than about 30 ppm, and in some instances about 34 ppm, which is higher than solvent extracted crude corn oil, which in some aspects can have sulfur and sulfur containing compounds in an amount of about 1 ppm to about 20 ppm. While corn contains some native sulfur content, primarily bound in the form of amino acids such as methionine, the majority of sulfur is contributed by chemical addition during the ethanol process. Both the amino acid form and the chemical forms, such as sulfates and sulfites, have a relatively high degree of solubility in water. Thus, in the process of recovering CSO, it is expected the various sulfur forms would be partially washed out with the CSO, and some residual sulfur content would remain in the CSO. Conversely these same water soluble sulfur compounds would not be easily extracted with non-polar solvents, such as hexane. Consequently, crude corn oil extracted by a solvent extraction process from corn DDG contain initial levels of sulfur and sulfur containing compounds in an amount of about 1 ppm to about 20 ppm, in some aspects less than about 15 ppm, in some aspects less than about 12 ppm, in some other aspects about 1 ppm to about 10 ppm, and in still other aspects about 1 ppm to about 5 ppm.

The CSO recovery process in ethanol plants relies on the concept of using an emulsifier to emulsify some of the free oil in water in order to help wash out additional oil from the stillage. An emulsion breaker such as flocculent may be used to separate the lipid and aqueous components into distinct phases in order to fully recover the CSO. Crude oil solvent extracted from DDGS, including crude corn oil solvent extracted from corn DDGS, have reduced contents of non-native emulsifiers and also flocculants (i.e., those used in the Nalco process). In some aspects, the crude oil solvent extracted from DDGS, including crude corn oil solvent extracted from corn DDGS, are substantially free of non-native emulsifiers and also flocculants. Crude oil solvent extracted from DDGS, including crude corn oil solvent extracted from corn DDGS, may also have a reduced content of acids and/or reaction products resulting from the classic method of decreasing pH to break an emulsion. In some aspects, crude oil solvent extracted from DDGS, including crude corn oil solvent extracted from corn DDGS, is substantially free of acids and/or reaction products resulting from the classic method of decreasing pH to break an emulsion. In some aspects, the distillers meal of the present invention has a reduced residual content of any chemicals used for enhanced recovery of oil from stillage including one or more emulsifiers and/or flocculants, which are soluble in solvent and/or oil. In some aspects, a non-polar solvent extraction reduces residual levels of such chemicals to levels of about 50% less than DDGS, in some aspects about 75% less, and in some aspects about 90% less, than DDGS that has not been solvent extracted but has been subjected to CSO recovery using such chemicals. During the CSO recovery process, an emulsifier may be used to help enhance the removal of oil from spent grains, and a flocculent may be used to further help recover oil from thin stillage after mechanical separation.

Distillers Meal

The distillers meal produced by a solvent extraction method as described herein retain desired nutritional properties. The solvent extraction process applied to the DDGS may be chosen and tailored to provide a distillers meal that exhibits nutritional properties suitable for animal feed applications. For example, in one embodiment, the DDGS are subjected to a solvent extraction process that provides distillers meal that retains substantially all the crude protein and fiber content of the DDGS prior to solvent extraction. In another embodiment, the distillers meal is corn distillers meal that retains substantially all of the crude protein and fiber content of the DDGS prior to solvent extraction. In yet another embodiment, distillers meal is corn distillers meal that retains substantially all of the crude protein and fiber content of the DDGS prior to solvent extraction and is the product of a hexane extraction process conducted on corn DDGS produced by a dry-grind corn ethanol biorefinery.

For example, where the DDGS are corn DDGS and the solvent extraction process is a hexane extraction, the biorefining and solvent extraction processes may be controlled to provide corn distillers meal having the following nutrient content by weight on a dry matter basis: about 28% to about 35% crude protein; about 4% to about 6% total nitrogen; about 1% to about 5% crude fat; about 4% to about 6% ash; about 5% to about 7% crude fiber; about 11.5% to about 16.5% acid detergent fiber; about 25% to about 35% neutral detergent fiber; about 50% to about 55% nitrogen free extract; about 75% to about 80% total digestible nutrients ("TDN"); or a combination of two or more of any of the forgoing nutritional properties. In another embodiment, where the DDGS are corn DDGS and the solvent extraction process is a hexane extraction, the biorefining and solvent extraction processes may be controlled to provide corn distillers meal exhibiting about 0.80 to about 0.85 Mcal/lb net energy lactation (NE/Lactation), about 0.85 to about 0.89 Mcal/lb net energy maintenance (NE/maintenance), about 1200 to about 1250 kcal/lb of metabolizable energy, or about 0.55 to about 0.60 Mcal/lb of net energy gain (NE/gain), or any combination of two or more such characteristics.

It is contemplated that where the DDGS are corn DDGS and the solvent extraction process utilizes other solvents or mixtures of solvents containing alkanes, the biorefining and solvent extraction process may be controlled to provide corn distillers meal having the following nutrient content by weight on a dry matter basis: about 28% to about 35% crude protein; about 4% to about 6% total nitrogen; about 1% to about 5% crude fat; about 4% to about 6% ash; about 5% to about 7% crude fiber; about 11.5% to about 16.5% acid detergent fiber; about 25% to about 35% neutral detergent fiber; about 50% to about 55% nitrogen free extract; about 75% to about 80% total digestible nutrients ("TDN"); or a combination of two or more of any of the forgoing nutritional properties. In another embodiment, where the DDGS are corn DDGS and the solvent extraction process is a hexane extraction, the biorefining and solvent extraction processes may be controlled to provide corn distillers meal exhibiting about 0.80 to about 0.85 Mcal/lb net energy lactation (NE/Lactation), about 0.85 to about 0.89 Mcal/lb net energy maintenance (NE/maintenance), about 1200 to about 1250 kcal/lb of metabolizable energy, or about 0.55 to about 0.60 Mcal/lb of net energy gain (NE/gain), or any combination of two or more such characteristics.

The distillers meal may be further processed, as desired, to provide a distillers meal product having desired characteristics, such as, for example, a desired flowabilty or density. Moreover, the distillers meal may be further processed to provide a product that is more easily packaged and distributed as an ingredient in a feed. Even further, the distillers meal may be processed to incorporate additional constituents to increase the feeding paltability or nutritional quality. For example, in one embodiment, the distillers meal may be further processed to incorporate a salt or a syrup from another manufacturing process that provides additional protein content. In another embodiment, the distillers meal may be pelleted to provide a feed material that is more readily packaged for sale and transport and is more easily incorporated into or used as an animal feed. For instance, Example 2 provides a description of an embodiment of corn distillers meal according to the description provided herein, as well as suitable process conditions for pelletizing the corn distillers meal described therein. Tables presented in Example 2 set out the process conditions under which the corn distillers meal was pelletized, describe a selection of physical properties exhibited by the non-pelleted and the pelleted corn distillers meal, and highlight a selection of nutritional properties exhibited by the non-pelleted and the pelleted corn distillers meal.

In some aspects, the solvent extracted crude oil from DDGS enhances the nutritional profile of the distillers meal by increasing the percentage of protein and amino acids contained in the distillers meal. For example, conventional corn DDGS having a corn oil content of about 10% typically has a lysine content of about 0.75% by weight on a dry matter basis. In comparison, corn distillers meal of the present invention that has a residual corn oil content of about 2% has a lysine content of about 0.81% by weight on a dry matter basis. This increase in lysine content in the corn distillers meal, when compared to the ratio of residual fat, results in a lysine to residual fat ratio percentage (% lysine/% residual fat)*100 of about 7.5 for conventional corn DDGS, as compared to a lysine to residual fat ratio of about 40.5 for corn distillers meal of the present invention.

In some aspects, the lysine content of corn distillers meal ranges from about 0.7% to about 1.0% for corn distillers meal having a residual fat content between about 0.5% to about 3.0%. As a result, the lysine to residual fat ratio for corn distillers meal is between about 23.3 to about 140 at a lysine content of about 0.7%, between about 26.7 and about 160 at a lysine content of about 0.8%, between about 30 and about 180 at a lysine content of about 0.9%, and between about 33.3 and about 200 at a lysine content of about 1.0%. Thus, corn distillers meal of the present invention may have a lysine to residual fat ratio between about 20 to about 200, in some aspects about 25 to about 180, in some aspects about 30 to about 160, and in some other aspects about 40 to about 140, with other ranges and subranges of the foregoing ranges contemplated herein. In comparison to an ethanol plant employing the CSO recovery method, and assuming a high native lysine content of about 0.9% and a residual fat content of about 4%, the lysine to residual fat ratio would at the very most be about 20.

When one or more of the specific fatty acids in the residual fat composition of the corn distillers meal are considered as opposed to the total residual fat, such as linoleic acid (C18:2) or oleic acid (C18:1), the ratios are further enhanced. For example, in the situation of linoleic acid, which is about 45% to about 60% of the total fatty acid content, and for the sake of this example assumed to be 50%, the lysine to linoleic acid ratio in corn distillers meal is in the range of about 46.6 to about 280 at a lysine content of about 0.7%, between about 53.4 and about 320 at a lysine content of about 0.8%, between about 60 and about 360 at a lysine content of about 0.9%, and between about 66.6 and about 400 at a lysine content of about 1.0%. Thus, corn distillers meal of the present invention may have a lysine to residual linoleic acid ratio between about 45 to about 400, in some aspects about 50 to about 360, in some aspects about 60 to about 320, and in some other aspects about 80 to about 280, with other ranges and subranges of the foregoing ranges contemplated herein. In comparison to an ethanol plant employing the CSO recovery method, and assuming a high native lysine content of about 0.9% and a residual fat content of about 4%, the lysine to residual linoleic acid ratio would at the very most be about 40.

When oleic acid is used as the specific fatty acid instead of the total residual fat or linoleic acid, the ratios are even further enhanced. For example, in the situation of oleic acid, which is about 20% to about 40% of the total fatty acid content, and for the sake of this example assumed to be 25%, the lysine to oleic acid ratio in corn distillers meal is in the range of about 85 to about 560 at a lysine content of about 0.7%, between about 105 and about 640 at a lysine content of about 0.8%, between about 120 and about 720 at a lysine content of about 0.9%, and between about 125 and about 800 at a lysine content of about 1.0%. Thus, corn distillers meal of the present invention may have a lysine to residual oleic acid ratio between about 85 to about 800, in some aspects about 105 to about 720, in some aspects about 120 to about 640, and in some other aspects about 160 to about 560, with other ranges and subranges of the foregoing ranges contemplated herein. In comparison to an ethanol plant employing the CSO recovery method, and assuming a high native lysine content of about 0.9% and a residual fat content of about 4%, the lysine to residual linoleic acid ratio would at the very most be about 40.

Conventionally, the protein content percentage in meals, such as flours, grains and oilseeds, is defined as the total nitrogen times 6.25, for example 1% total nitrogen equals 6.25% protein. In conventional DDGS, including corn DDGS, the ratio of total nitrogen to total free fatty acids is less than 25. In distillers meal of the present invention, including corn distillers meal, the ratio of total nitrogen to total free fatty acids is greater than 25 up to about 200, in some aspects about 35 to about 200, and still in other aspects about 50 to about 200. In some aspects of the present invention, the total free fatty acid content in solvent extracted oil is about 2% to about 10%, in some aspects about 3% to about 9%, and in some aspects about 5% to about 8%, and in some further aspects about 7% to about 8%. In comparison, the fatty acid content resulting from the CSO recovery method would be inherently higher due to the hydrolytic splitting of the oil in the presence of water required for the CSO recovery method. As such, a free fatty acid content of about 10% or even higher for the CSO recovery method is not unusual.

Crude oil that is solvent extracted from DDGS, including crude corn oil that is solvent extracted from corn DDGS, may also be substantially free of non-native emulsifiers and also flocculants (i.e., Nalco process). Crude oil solvent extracted from DDGS, including crude corn oil solvent extracted from corn DDGS, are also substantially free of acids and/or reaction products resulting from the classic method of decreasing pH to break an emulsion. In comparison, the CSO recovery process in ethanol plants relies on the concept of using an emulsifier to emulsify some of the free oil in water in order to help wash out additional oil from the stillage.

Further Processing of the Crude, Extracted Oil

After extraction from the DDGS, the crude oil may be further processed as desired. For example, the crude oil may be filtered, degummed, neutralized, bleached and/or deodorized to provide a food grade oil for consumer use. For example, in one embodiment, the crude oil may be degummed, caustic refined, and subjected to a soap removal step according to commercially available processes, such as water washing. Following these steps the oil may then be subjected to one or more clay bleaching steps to achieve an oil of desired content and color. Where one or more clay bleaching steps are used, the clay may be an acid activated clay or a non-acid activated clay, a silica based product, other adsorptive filtration media and/or combinations thereof and may include, by way of example, an acid activated clay or a non-acid activated clay at 0.1%-1%, 1-5%, 2-4%, or 2-3%. In addition to or as an alternative to clay bleaching, after the crude oil has been degummed, caustic refined and subjected to a soap removal step, a food grade oil of a desired color, very low free fatty acid content, improved flavor and improved stability may be achieved using a deodorization step whereby thermal decomposition of color bodies and removal of volatile components takes place under high temperature and high vacuum. Suitable processes for degumming, caustic refining, and soap removal are also described herein in relation to the pretreatment steps for biodiesel and glycerine production from the crude oil. Degumming, neutralization, bleaching and/or deodorization are also accessible to those of skill in the art and can be utilized as described herein to achieve a food grade oil and industrial grade oils.

Figure 2:
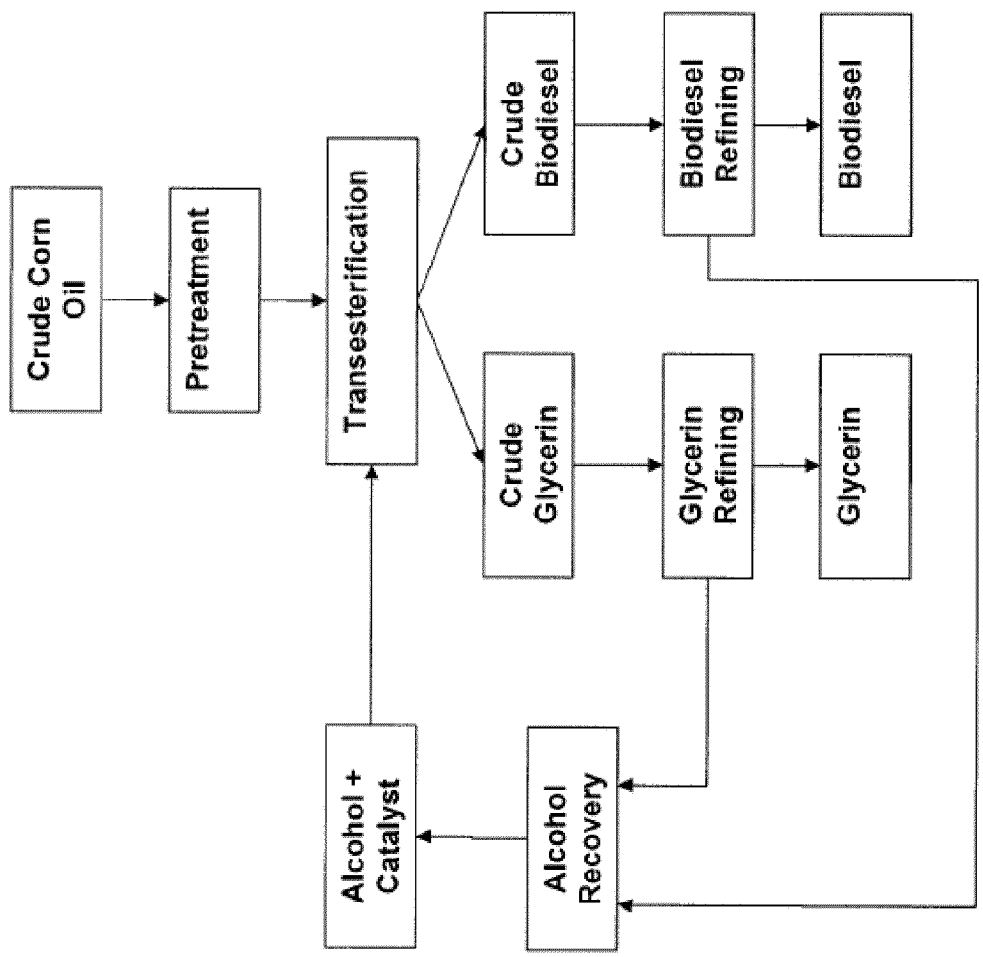
FIG. 2 provides a flow-chart representation of the process by which biodiesel and glycerine are produced from oil extracted from DDGS.

Alternatively, the crude oil extracted from DDGS may be used to produce biodiesel and glycerine. A flow-chart representation of a process for refining biodiesel and glycerine from the crude extracted oil is shown in FIG. 2. There are several processes that may be used to produce biodiesel from oils and fats, including base catalyzed transesterification, direct acid catalyzed transesterification and/or esterification, enzyme catalyzed transesterification and/or esterification, high pressure transesterification (i.e. Henkel process), and/or a combination of same for conversion of the oil to biodiesel. Biodiesel production technologies and equipment are commercially available from, for example, Crown Iron Works Company of Minneapolis, Minn., U.S.A., and from Lurgi AG of Frankfurt, Germany. To produce biodiesel and glycerine from the crude oil extracted from the DDGS, an acid catalyzed esterification or caustic neutralization, followed by a transesterification process may be used.

In one embodiment, of the refining process outlined in FIG. 2, the crude extracted oil is crude corn oil, and before the crude corn oil is subjected to a transesterification process, it may be pretreated. Pretreatment of the crude corn oil may be carried out, for example, to remove gums included in the oil or to remove or neutralize free fatty acids. As part of a degumming process, an acid, such as phosphoric acid, may be added to the crude corn oil and the crude oil may be heated, for example, using steam. In such a process, the acid and steam work to hydrate the gums so that the gums can be separated from the crude corn oil, such as by centrifugation or another suitable separation technique.

Free fatty acids in the crude corn oil are generally undesirable because they form soaps within the oil as they react with the base catalyst used to drive the transesterification reaction. If the crude corn oil is also pretreated with a degumming step, the addition of the strong base intended to neutralize the free fatty acids may occur after addition of the acid in the degumming step. In this manner, the base added to neutralize the free fatty acids can also work to neutralize the acid used in the degumming step. The soap stock that results from degumming and neutralization of the crude corn oil may be separated from the corn oil using standard equipment, such as a centrifugal separator. Alternatively, the free fatty acids can be removed and acid esterified to form biodiesel, or combined with glycerine to form triglycerides, which are then transesterified to form biodiesel.

Treatment of the crude corn oil may also include one or more bleaching steps, such as one or more heat bleaching or clay bleaching steps as described above, to remove residual color or other impurities from the corn oil.

Where pretreatment of the crude corn oil includes degumming and neutralization of free fatty acids, prior to a transesterification process, the degummed and neutralized oil is typically washed prior to transesterification. Washing may include, for example, mixing the pretreated corn oil with warm wash water. After washing, the oil and wash water are separated, and the pretreated corn oil is dried, such as by a vacuum-dryer, to a desired water content.

In one embodiment, the pretreated corn oil can be subjected to a transesterification reaction to provide biodiesel and glycerine. The transesterification reaction is based on the chemical reaction of triglycerides contained in the crude corn oil with an alcohol in the presence of an alkaline catalyst. The alkaline catalyst used in the transesterification reaction may be selected from several different alkaline materials. Suitable catalysts are strong bases and include, for example, NaOH (caustic soda), KOH (potash), and $CH_3NaO$ (sodium methylate). The alcohol used in the transesterification reaction may be selected from, for example, methanol or ethanol.

As the transesterification reaction is carried out, the alcohol and catalyst may be delivered into the corn oil in parallel, as separate reaction components, or the alcohol and catalyst can be delivered to the crude corn oil as a mixture. When delivered as a mixture, the catalyst may be dissolved in the alcohol by any suitable means prior to charging the mixture into the corn oil. Alternatively, the catalyst may be provided as a liquid and mixed with the alcohol, limiting the need for dissolution of the catalyst in the alcohol prior to mixing the alcohol and catalyst with the corn oil. Where the catalyst is mixed with the alcohol as a liquid, the catalyst may be added to the alcohol by, for example, one or more metering pumps. In addition, because an alkaline catalyst might be sensitive to water, the catalyst may be stored in a pump tank protected with a nitrogen layer.

In carrying out the transesterification reaction, the alcohol, catalyst and corn oil may be charged into a closed reaction vessel. The reaction system can be closed to the atmosphere to prevent loss of the alcohol used in the transesterification reaction. As the reaction components are mixed, the mixture may be kept just below the boiling point of the alcohol to speed the reaction time. In addition, an excess amount of alcohol is typically used to ensure total conversion of the corn oil triglycerides into the desired ester product. The transesterification reaction produces a two-phase reaction product that includes an ester-rich phase (crude biodiesel) and a glycerine-rich phase (crude glycerine). The crude glycerine is much more dense than the crude biodiesel and the two phases can be easily separated by gravity separation or, if needed or desired, centrifugation.

In one embodiment, transesterification of the corn oil takes place in one or more mixer-settler units. In such units, the transesterification reaction occurs in a mixer or reactor included in the mixer-settler units. The crude biodiesel and crude glycerine resulting from the transesterification reaction form two distinct phases that can be separated in the settlers. If two or more mixer-settler units are used as the reaction vessels, the feedstock and the intermediate product, respectively, may flow successively through the two or more mixer-settler units. Each mixer-settler unit can be supplied with the desired alcohol and catalyst in parallel. The reactors included in the mixer-settler units can be multi-stage in design, comprising various reaction chambers in order to achieve maximum conversion efficiency to the ester product. The settlers allow phase separation to approach the limit of solubility, which eases downstream purification of the biodiesel and glycerine products.

At the transesterification stage, vapors vented from the reaction vessel, such as the one or more mixer-settlers, may be routed to a condenser where they are partly or completely condensed and returned to the reaction process. The same may be done with the vessel used to store or deliver the alcohol used in the transesterification reaction. Even further, where the catalyst is provided in liquid form, it too may be stored and delivered from a storage vessel, and any vapors vented from the catalyst storage vessel may also be captured, partly or completely condensed, and returned to the reaction process in liquid form.

Once the transesterification reaction is complete, two major products exist: glycerine and biodiesel. The glycerine is included in the crude glycerine phase and the biodiesel is incorporated in the crude biodiesel phase. Each of these crude phases may include a substantial excess of the alcohol used in the reaction. Moreover, the crude reaction products may include other impurities such as excess catalyst, soaps and high boiling impurities. If desired, some of these impurities may be treated or removed from the crude reaction products before the crude biodiesel and the crude glycerine phases are separated. For example, a suitable acid may be added to and mixed with the reaction products to neutralize excess catalyst and further help break any emulsions. Additionally, excess alcohol may be removed from the crude reaction products using standard distillation equipment and techniques.

After the crude biodiesel and crude glycerine are separated, they are typically subjected to further refining. For example, after separation, the crude biodiesel may contain residual alcohol, glycerine, small amounts of catalyst, and soaps. This may be the case even if the crude reaction products are refined to remove or neutralize impurities prior to separation. If they have not already been refined to neutralize excess catalyst or remove excess alcohol, or if residual catalyst and excess alcohol still remain in the separated reaction products, the crude biodiesel and crude glycerine may be treated with a suitable acid to neutralize the residual catalyst and subjected to, for example, a flash evaporation process or distillation to remove the excess alcohol.

Even where steps are taken to neutralize residual catalyst and remove excess alcohol, the refined biodiesel may still include water soluble impurities. In order to remove such water-soluble substances, the refined biodiesel may be washed and dried. To avoid the formation of emulsions during washing, the biodiesel may be pH adjusted, for example, by the addition of an acid to the biodiesel to be washed. Dilute HCl, such as a 3.7% strength HCl, is suitable for such an application and can be prepared and added as necessary. The biodiesel wash process may simply include gentle mixing of the biodiesel with warm water, which will work to remove residual, water soluble impurities as they are taken up in the aqueous phase.

If the biodiesel is processed through such a washing step, the refined and washed biodiesel may contain excess water. Such excess water may be removed, for example, by subjecting the biodiesel to a drying step. The drying step may include, for example, vacuum drying the biodiesel to a desired water content in a dryer circuit. The dried biodiesel, which is ready for use, distribution or sale, is collected and stored. Though the biodiesel is serviceable at this point, if desired, it can be subjected to further distillation to remove any color bodies and other higher molecular weight impurities remaining to provide a colorless biodiesel.

The separated, crude glycerine phase may also be further refined after separation. In particular, the crude glycerine may be neutralized with a suitable acid, the excess alcohol may be removed by distillation or flash evaporation, and the crude glycerine may be dried to remove residual water. Even if the crude reaction products of the transesterification process are neutralized and the excess alcohol present in the crude reaction products is removed prior to separation, the separated, crude glycerine may still contain residual catalyst or alcohol. Where that is the case, the separated, crude glycerine may be subjected to additional neutralization, absorbtive filtration, and/or distillation steps to neutralize any residual catalyst and remove any remaining alcohol. Once such neutralization, distillation and drying steps are complete, the crude product typically contains approximately 80-88% pure glycerine. This crude glycerine can be further refined to a purity of 99% or higher, as is known in the art, such that the glycerine product is suitable for use in cosmetic or pharmaceutical applications.

In order to minimize loss of the alcohol used in the transesterification reaction, all vessels which contain alcohol, whether in substantially pure form or as part of a crude reaction product, may be connected to a vent system to capture any alcohol vapors. Captured alcohol vapors may be fed into a condensing system that recovers the alcohol and recycles the alcohol back into the refining process.

Figure 3A:
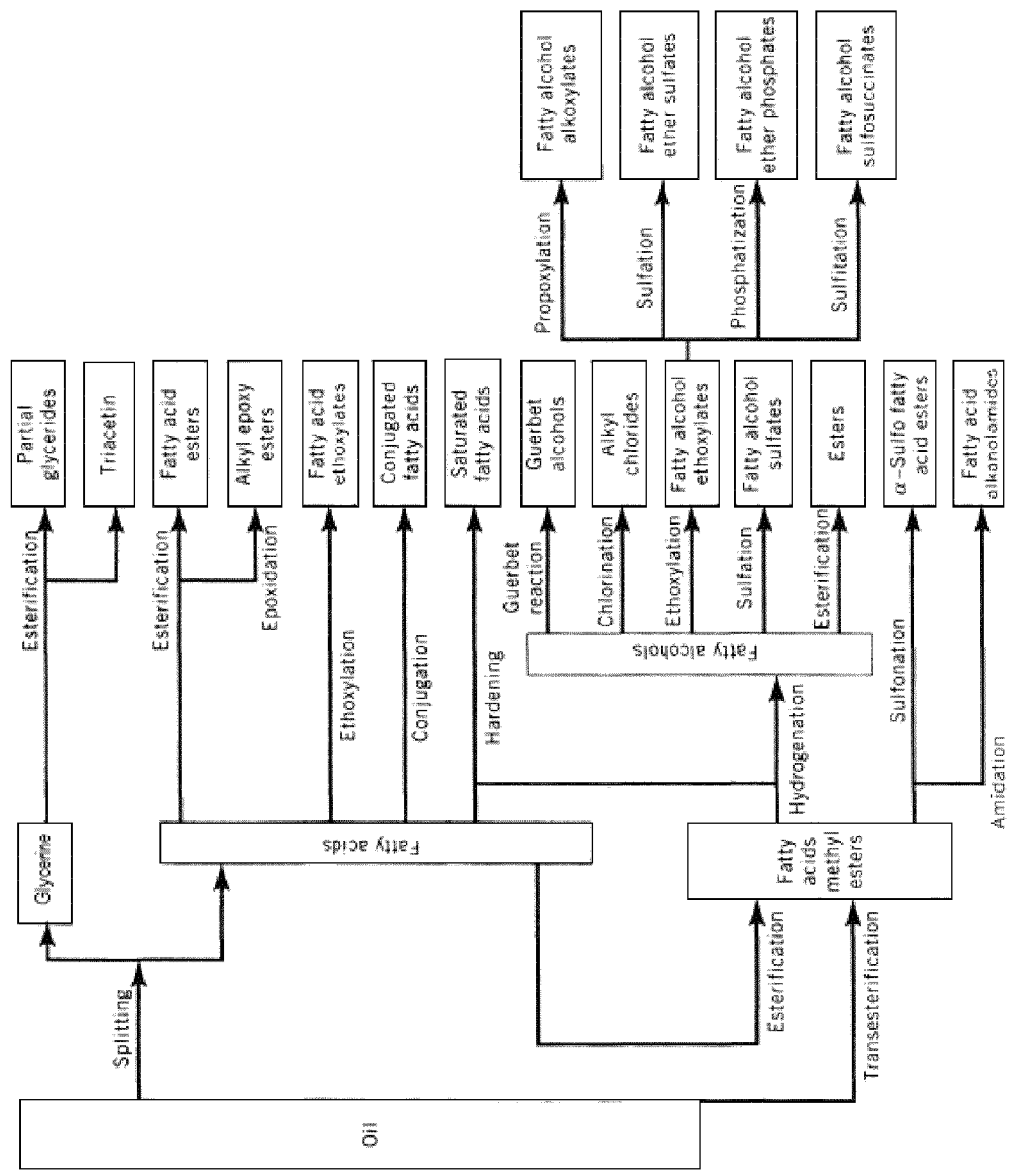
FIGS. 3A and 3B provides a flow-chart representation of the oleochemical production processing using oil extracted from DDGS and/or DDG according to certain aspects of the present invention.
Figure 3B:
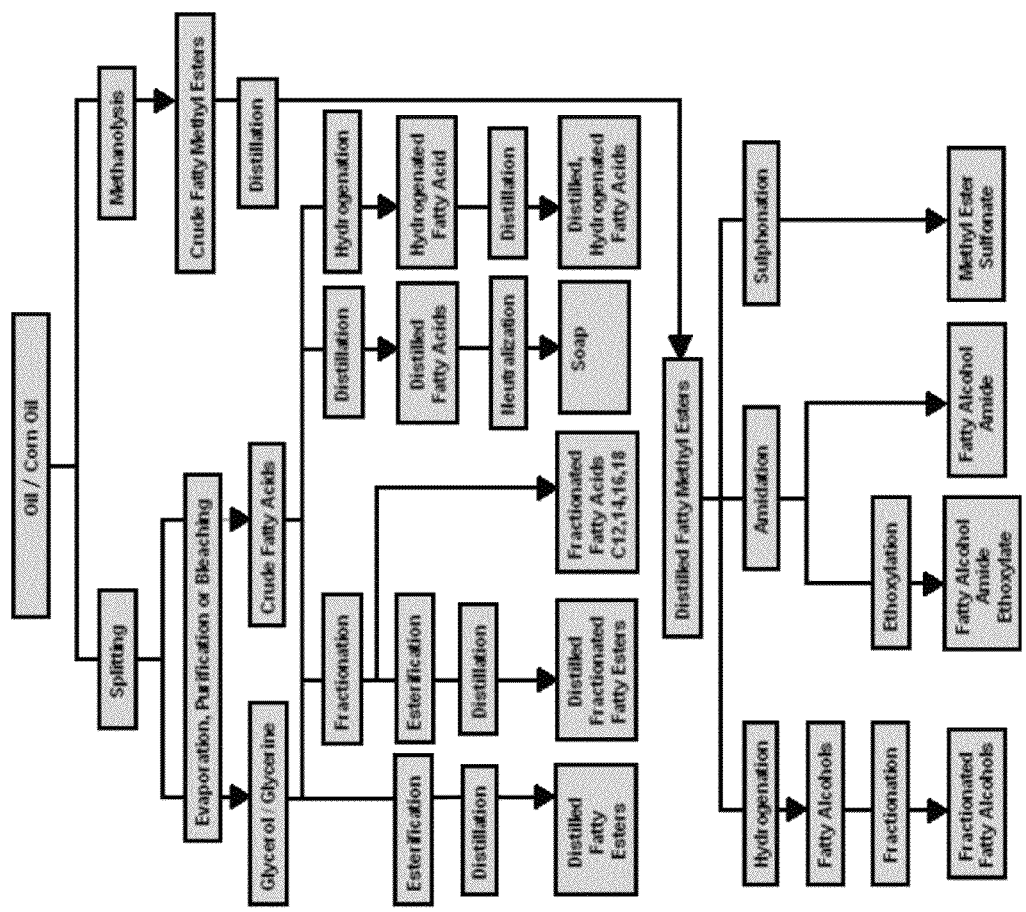

Still alternatively, the crude oil extracted from DDGS may be used to produce other oleochemicals, particularly oleochemicals for the personal care products and home care products industries. A flow-chart representation of oleochemical processing of crude oil extracted from DDGS is shown in FIG. 3. There are several processes that may be used to produce various oleochemicals after the crude oil undergoes a splitting (or hydrolysis) process of the triglycerides into crude fatty acids and glycerol/glycerine, followed by additional processing including esterification, fractionation, distillation, hydrogenation, epoxidation, ethoxylation, conjucation, hardening, chlorination and/or sulfation. After the splitting process, additional processing may be utilized prior to such processes, including evaporation, purification and/or bleaching to produce glycerol/glycerine and crude fatty acids. The crude fatty acids and/or glycerine can be subjected to further chemical and enzymatic reactions to produce desired oleochemicals for personal care products and home care products.

In some aspects, the glycerine is subjected to esterification and distillation processing to yield distilled fatty esters of glycerine.

In some aspects, the crude fatty acids are subjected to esterification processing to yield fatty acid esters, esterification and distillation processing to yield distilled fractionated fatty esters, and/or esterification and epoxidation processing to yield alkyl epoxy esters. In some aspects, the crude fatty acids are subjected to ethoxylation processing to yield fatty acid ethoxylates. In some aspects, the crude fatty acids are subjected to conjugation processing to yield conjugated fatty acids. In some aspects, the crude fatty acids are subjected to hardening processing to yield saturated fatty acids. In some aspects, the crude fatty acids are subjected to hardening processing and then hydrogenation processing to yield fatty alcohols. In some aspects, the crude fatty acids are subjected to esterification processing to yield fatty acids methyl esters and then hydrogenation to yield fatty alcohols. In some aspects, the fatty alcohols derived from fatty acids may then be subjected to Guerbet reaction to yield Guerbet alcohols, chlorination to yield alkyl chlorides, ethoxylation to yield fatty alcohol ethoxylates, sulfation to yield fatty alcohol sulfates and/or esterification to yield esters. The fatty alcohol ethoxylates may further under propoxylation to yield fatty alcohol alkoxylates, sulfation to yield fatty alcohol ether sulfates, phosphatization to yield fatty alcohol ether phosphates and/or sulfitation to yield fatty alcohol sulfosuccinates. In some aspects, the crude fatty acids are subjected to fractionation processing to yield C12, C14, C16 and/or C18 fractionated fatty acids, with the remaining fraction subjected to esterification and distillation to yield distilled fractionated fatty esters.

Examples of common personal care ingredients ultimately derived from these fatty acids according to aspects of the present invention may include octyl stearate, glyceryl stearate, PEG distearate and stearalkonium chloride. Examples of materials used in producing home care products ultimately derived from these fatty acids according to aspects of the present invention may include sulfonated methyl esters and stearyl alcohol.

Figure 4:
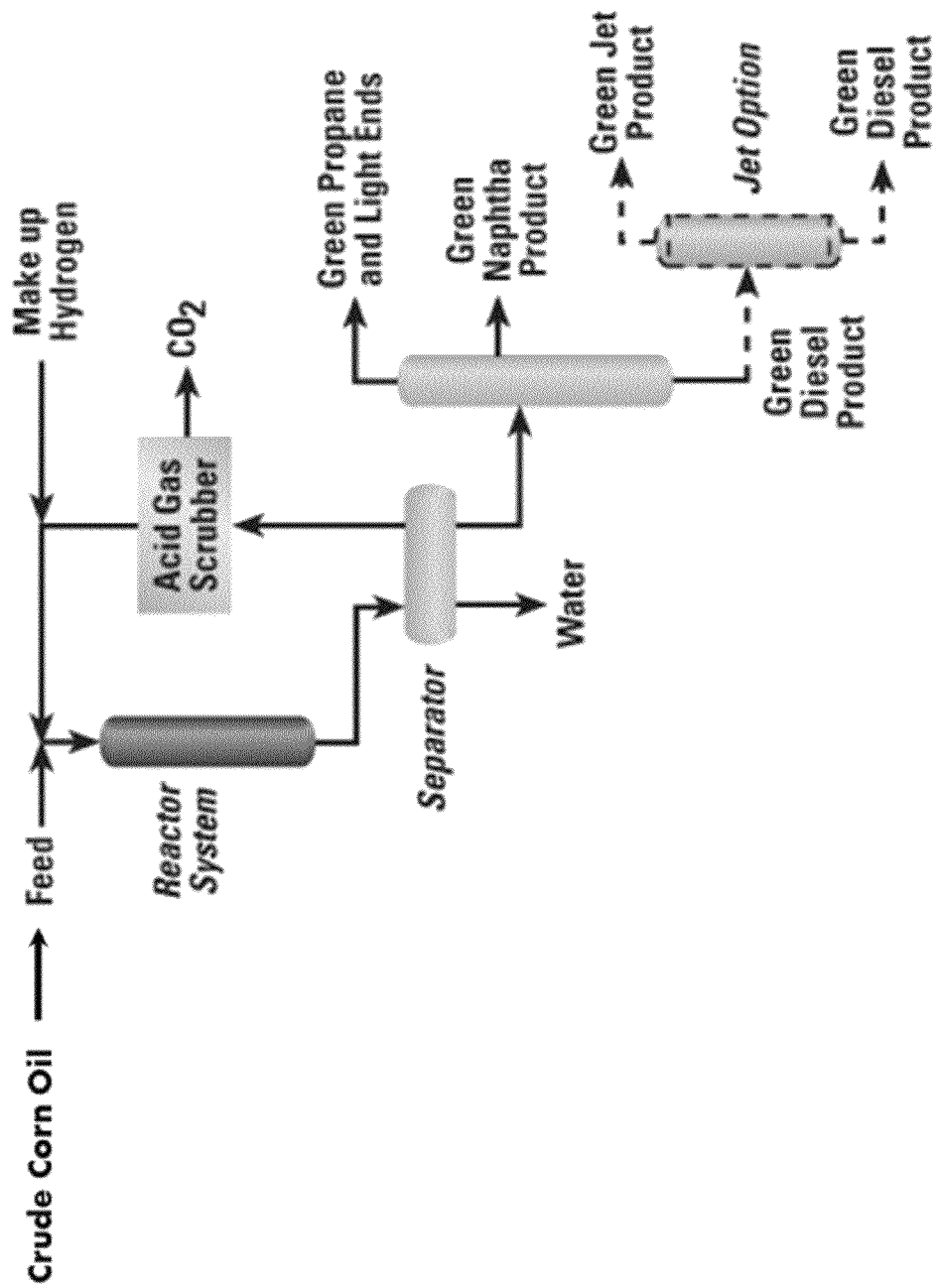
FIG. 4 provides a flow-chart representation of the renewable diesel production process using oil extracted from DDGS and/or DDG according to certain aspects of the present invention.

Still alternatively, the crude oil extracted from DDGS may be used to produce a green renewable diesel fuel. As illustrated in FIG. 4, the crude oil extracted from DDGS may be subjected to a hydro-treating process, which involves the hydrogenation of the double bonds of the side chains of the triglycerides in the crude oil extracted from DDGS and the removal of oxygen on the metal sites of the catalysts. The hydro-treating of the crude oil extracted from DDGS leads to the production of C14-C20 hydrocarbons, which is a liquid mixture with the boiling point range of diesel.

In the hydro-treating process, crude oil extracted from DDGS is the feedstock, which may be mixed with recycle hydrogen and/or make-up hydrogen before being provided at process pressure in a reactor system comprising one or more catalytic hydrodeoxygenation reactors. In some aspects, the reactor is a multi-stage adiabatic, catalytic hydrodeoxygenation reactor. In the reactor, the crude oil extracted from DDGS is saturated and completely deoxygenated to yield deoxygenated hydrocarbon products. The primary deoxygenation reaction by-products are propane, water and carbon dioxide, which along with other low molecular weight hydrocarbons may be separated from the deoxygenated product. In some aspects, the deoxygenated product is processed in a second reactor packed with a selective hydrocracking catalyst where both cracking of larger molecules and hydroisomerization takes place. In some aspects, the deoxygenated product is mixed with additional hydrogen gas for the hydroisomerization process. The excess hydrogen and the isomerized product may be separated in a conventional gas/liquid separator. The resulting product then undergoes separation in a fractional distillation column where the various products are produced, including green propane and light ends, green naptha product, and green diesel product. The green diesel product may include a green jet product and a green diesel product. The hydro-treating process for producing green diesel operates in mild conditions and integrates well within existing petroleum refineries. In some aspects, the hydro-treating process can be conducted onsite at an ethanol facility.

Distillers Meal as an Animal Feed or Animal Feed Supplement

DDGS are often used as a feed supplement for livestock and poultry fed high grain content finishing diets. Before solvent extraction, DDGS may have approximately 30% by weight crude protein ("CP") and 20% crude fiber ("CF"). Solvent extraction as described herein removes most of the oil from the DDGS so that such oil can be processed or refined to provide additional products of commercial value. However, because most of the oil present in DDGS is removed in producing distillers meal, the energy potential of the distillers meal from the fat content is lower than that exhibited by the DDGS prior to solvent extraction. Despite the lower energy potential resulting from oil extraction, distillers meal as described herein provides a high-quality, low-cost protein feed that can be fed at higher inclusion rates for animals, such as domestic pets, livestock or poultry. In addition, as described herein, livestock feed distillers meal exhibit desirable carcass traits, and the nutritional properties of distillers meal may provide a superior feed or feed supplement.

In one embodiment, the distillers meal disclosed herein may be used to supplement animal diets at a desired percentage of the total diet, on a dry matter basis. In one embodiment, the distillers meal may be used as a CP supplements in livestock and poultry feed diets. In addition, the distillers meal described herein may also be used as an animal feed or feed supplement that provides desired amounts of carbohydrates, fiber or non-protein nitrogen (NPN) containing compounds. The distillers meal can be used at a percentage of the total feed that maximizes the nutritional components of the feed. The relative amount of distillers meal incorporated into an animal diet may depend on, for example, the species, sex, or agricultural use of the animal being fed. Additionally, the relative amount of distillers meal incorporated into a particular diet may depend on the nutritional goals of the diet.

In one embodiment, distillers meal may be used to provide approximately 50% to approximately 75% by weight, on a dry matter basis, of a total diet for use in an animal feed. In one such embodiment, the distillers meal is corn distillers meal as described herein and is used to provide approximately 50% to 55%, 50% to 60%, 50% to 65%, or 50% to 70% by weight, on a dry matter basis, of the total diet. In some aspects, the distillers meal is substituted in an animal feed diet for soybean meal, corn, DDGS and/or other protein supplements in rations for such animal. In another such embodiment, the distillers meal is corn distillers meal as described herein and is used to provide approximately 50% to 55%, 55% to 60%, 55% to 70%, 60% to 65%, 60% to 70%, or 70% to 75% by weight, on a dry matter basis, of the total diet. In some aspects, the corn distillers meal is substituted in an animal feed diet for soybean meal, corn, DDGS and/or other protein supplements in rations for such animal.

In another embodiment, distillers meal as described herein may be used to provide approximately 0 to 5%, approximately 5% to 10%, approximately 5% to 15%, approximately 5% to 25%, approximately 5% to 30%, approximately 10% to 15%, approximately 15% to 20%, approximately 20% to 25%, approximately 25% to 30%, approximately 30% to 35%, approximately 35% to 40%, approximately 40% to 45%, or approximately 45% to 50% by weight, on a dry matter basis, of a total animal diet. In one such embodiment, distillers meal as described herein is used as a CP supplement in a cattle diet, and the distillers meal provides approximately 5% to 20% by weight, on a dry matter basis, of the total diet. In yet another such embodiment, distillers meal as described herein is used as a CP supplement in a cattle diet, and the distillers meal provides approximately 5% to 15% by weight, on a dry matter basis, of the total diet. In still yet another such embodiment, distillers meal as described herein is used as a CP supplement in a cattle diet, and the distillers meal provides approximately 10% to 15% by weight, on a dry matter basis, of the total diet. In yet another such embodiment, distillers meal as described herein is used as a CP supplement in a cattle diet, and the distillers meal provides approximately 10% to 12% by weight, on a dry matter basis of the total diet. In another such embodiment, distillers meal as described herein is used as a CP supplement in a cattle diet, and the distillers meal provides approximately 7% to 12% by weight, on a dry matter basis, of the total diet. In each of the preceding embodiments, where the distillers meal is fed to cattle, the distillers meal may be corn distillers meal as described herein and the cattle may be finishing cattle.

In another embodiment, distillers meal as described herein may be used in feeding dairy cattle. Where corn distillers meal is used as a dairy cattle feed, it may be provided at, for examples, up to approximately 30%, approximately 5% to 30%, approximately 5% to 25%, approximately 5% to 20%, approximately 5% to 15%, approximately 10% to 15%, approximately 15% to 20%, approximately 15% to 25%, approximately 15% to 30%, approximately 10% to 20%, approximately 10% to 25%, approximately 20% to 25%, or approximately 25% to 30% by weight, on a dry matter basis, of the total diet. In each of the exemplary embodiments, where the distillers meal is fed to dairy cattle, the distillers meal may be corn distillers meal as described herein.

In another embodiment, distillers meal as described herein is used as a feed supplement for cattle to achieve a desired F/G ratio. As it is used herein, the term "F/G ratio" refers to the ratio of pounds of feed per pound of daily gain. In one embodiment, distillers meal as described herein is used as a cattle feed supplement to achieve an F/G ratio of 4.5 or less after 4 weeks of feeding. In another embodiment, distillers meal as described herein is used as a cattle feed supplement to achieve an F/G ratio of 5.0 or less after 8 weeks of feeding. In yet another embodiment, distillers meal as described herein is used as a cattle feed supplement to achieve an F/G ratio of 6.5 or less after 12 weeks of feeding. In yet another embodiment, distillers meal as described herein is used as a cattle feed supplement to achieve an F/G ratio of 7.0 or less after 16 weeks of feeding. In yet another embodiment, distillers meal as described herein is used as a cattle feed supplement to achieve an F/G ratio of 6.5 or less through 18 weeks of feeding. In each of the embodiments described herein pertaining to use of distillers meal as a feed supplement in cattle to achieve a desired F/G ratio, the distillers meal may be corn distillers meal, the cattle may be, for example, finishing cattle, and the corn distillers meal may provide, for example, approximately 5% to 15%, 5% to 10%, 7%-12%, or 10% to 12% by weight, on a dry matter basis, of the total diet. Alternatively, in each of the embodiments described herein pertaining to use of distillers meal as a feed supplement in cattle to achieve a desired F/G ratio, the distillers meal may be corn distillers meal, the cattle may be, for example, finishing cattle, and the corn distillers meal may provide, for example, approximately 5%, 6%, 7%, 8%, 9%, 10%, 11%, 12%, 13%, 14%, or 15% by weight, on a dry matter basis, of the total diet.

In yet another embodiment, distillers meal as described herein may be used as a feed supplement for cattle to achieve a desired average daily gain (ADG). In one embodiment, distillers meal as described herein is used as a cattle feed supplement to achieve an ADG of 4.0 lbs or greater after 4 weeks of feeding. In another embodiment, distillers meal as described herein is used as a cattle feed supplement to achieve an ADG of 4.5 lbs or greater after 8 weeks of feeding. In yet another embodiment, distillers meal as described herein is used as a cattle feed supplement to achieve an ADG of 3.5 lbs or greater after 12 weeks of feeding. In yet another embodiment, distillers meal as described herein is used as a cattle feed supplement to achieve and maintain an ADG of 3.5 lbs or greater through 16 weeks of feeding. In yet another embodiment, distillers meal as described herein is used as a cattle feed supplement to achieve and maintain an ADG of 3.5 lbs or greater through 18 weeks of feeding. In yet another embodiment, distillers meal as described herein is used as a cattle feed supplement to achieve an ADG of 4.0 lbs or greater after 18 weeks of feeding. In each of the embodiments described herein pertaining to use of distillers meal as a feed supplement in cattle to achieve a desired ADG, the distillers meal may be corn distillers meal, the cattle may be, for example, finishing cattle, and the corn distillers meal may provide, for example, approximately 5% to 15%, 5% to 10%, 7%-12%, or 10% to 12% by weight, on a dry matter basis, of the total diet. Alternatively, in each of the embodiments described herein pertaining to use of distillers meal as a feed supplement in cattle to achieve a desired ADG, the distillers meal may be corn distillers meal, the cattle may be, for example, finishing cattle, and the corn distillers meal may provide, for example, approximately 5%, 6%, 7%, 8%, 9%, 10%, 11%, 12%, 13%, 14%, or 15% by weight, on a dry matter basis, of the total diet.

The distillers meal may be provided in meal form or in pellet form or other forms useful for feeding livestock or poultry, as would be recognized in the art. The distillers meal may also be premixed with other desired ingredients of a livestock or poultry diet and provided for use in a ready-to-feed form. In addition to distillers meal as described herein, livestock and poultry diets as described herein may further include, for example, desired percentages of other components such as feed corn, corn meal, soybean meal, urea, hay, pre-prepared cattle feeds, protein supplements, mineral supplements, liquid supplements and other feed components as known and used by those of skill in the art. Other acceptable materials used in livestock and poultry feed may include, for example, soybeans, soy hulls, soybean protein derivatives, wheat, wheat middling, wheat straw, alfalfa, sugar beet tailings, sugar beet pulp, sugar beets, corn stalks, corn cobs, popcorn husks, sweet bran, silage, meat and bone meal, molasses, oats, oat straw, barley, barley straw, sunflower seeds and hulls, milo, and wild grass, cottonseed by-products, such as delinted whole cottonseed, fuzzy cottonseed, and by-products of other oil seeds.

In some aspects, the distillers meal as described herein is used as a feed supplement or formula feed for beef cattle, including the beef cattle classes of calves, cattle on pasture and/or feedlot cattle. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a maximum percentage of equivalent crude protein from non-protein nitrogen of about 6%, in some aspects about 5%, and in some aspects about 4%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; a minimum percentage of phosphorous in an amount of about 0.7%, in some aspects about 0.75%, and in some other aspects about 0.8%; and a minimum percentage of potassium in an amount of about 0.8%, in some aspects about 0.85%, in some aspects about 0.9%, in some aspects about 0.95%, and in some other aspects about 1.0%.

In some aspects, the distillers meal as described herein is used as a feed supplement or feed formula for dairy cattle, particularly veal milk replacer and/or herd milk replacer. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; and a minimum percentage of phosphorous in an amount of about 0.8%, in some aspects about 0.85%, in some aspects about 0.9%, in some aspects about 0.95%, and in some other aspects about 1.0%.

In some aspects, the distillers meal as described herein is used as a feed supplement or feed formula for dairy cattle, particularly starter, growing heifers, bulls and dairy beef, lactating dairy cattle and/or non-lactating dairy cattle. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a maximum percentage of equivalent crude protein from non-protein nitrogen of about 6%, in some aspects about 5%, and in some aspects about 4%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a maximum percentage of acid detergent fiber in an amount of about 16.5%, in some aspects about 15.5%, in some aspects about 14.5%, in some aspects about 13.5%, in some aspects about 12.5%, and still in some other aspects about 11.5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; a minimum percentage of phosphorous in an amount of about 0.7%, in some aspects about 0.75%, and in some other aspects about 0.8%; and a minimum selenium in an amount below detection limits of about 2.25 ppm.

In some aspects, the distillers meal as described herein is used as a feed supplement or feed formula for equine, including foal, mare, breeding and/or maintenance equine. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; a minimum percentage of phosphorous in an amount of about 0.7%, in some aspects about 0.75%, and in some other aspects about 0.8%; a minimum amount of copper of about 3 ppm, in some aspects about 4 ppm, in some aspects about 5 ppm, in some aspects about 6 ppm; a minimum selenium in an amount below detection limits of about 2.25 ppm; and a minimum zinc of about 50 ppm, in some aspects about 55 ppm, in some aspects about 60 ppm, in some aspects about 65 ppm, in some aspects about 70 ppm, and in some other aspects about 75 ppm.

In some aspects, the distillers meal as described herein is used as a feed supplement or feed formula for swine, including pre-starter, starter, grower, finisher, gilts, sows and adult boars, lactating gilts and/or lactating sows. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a minimum percentage of lysine in an amount of about 0.7%, in some aspects about 0.75%, in some aspects about 0.8%, in some aspects about 0.85%, in some aspects about 0.9%, in some aspects about 0.95%, and in some other aspects about 1.0%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; a minimum percentage of phosphorous in an amount of about 0.7%, in some aspects about 0.75%, and in some other aspects about 0.8%; a minimum selenium in an amount below detection limits of about 2.25 ppm; and a minimum zinc of about 50 ppm, in some aspects about 55 ppm, in some aspects about 60 ppm, in some aspects about 65 ppm, in some aspects about 70 ppm, and in some other aspects about 75 ppm.

In some aspects, the distillers meal as described herein is used as a feed supplement or feed formula for poultry, including layer chickens (starting/growing, finisher, laying and/or breeder), broiler chickens (starting/growing, finisher and/or breeder), broiler breeder chickens (starting/growing, finishing and/or laying) and/or turkeys (starting/growing, finisher, laying and/or breeder). The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a minimum percentage of lysine in an amount of about 0.7%, in some aspects about 0.75%, in some aspects about 0.8%, in some aspects about 0.85%, in some aspects about 0.9%, in some aspects about 0.95%, and in some other aspects about 1.0%; a minimum percentage of methionine of about 0.50%, in some aspects about 0.55%, in some aspects about 0.60%, in some other aspects about 0.65%, and in some other aspects about 0.7%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; and a minimum percentage of phosphorous in an amount of about 0.7%, in some aspects about 0.75%, and in some other aspects about 0.8%.

In some aspects, the distillers meal as described herein is used as a feed supplement or feed formula for a goat, including starter, grower, finisher, breeder and/or lactating goats. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a maximum percentage of equivalent crude protein from non-protein nitrogen of about 6%, in some aspects about 5%, and in some aspects about 4%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; a minimum percentage of phosphorous in an amount of about 0.7%, in some aspects about 0.75%, and in some other aspects about 0.8%; a minimum amount of copper of about 3 ppm, in some aspects about 4 ppm, in some aspects about 5 ppm, in some aspects about 6 ppm, and a maximum amount of copper of about 10 ppm, in some aspects about 9 ppm, in some aspects about 8 ppm, in some aspects about 7 ppm, and in some other aspects about 6 ppm; and a minimum selenium in an amount below detection limits of about 2.25 ppm.

In some aspects, the distillers meal as described herein is used as a feed supplement or feed formula for sheep, including starter, grower, finisher, breeder and/or lactating sheep. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a maximum percentage of equivalent crude protein from non-protein nitrogen of about 6%, in some aspects about 5%, and in some aspects about 4%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; a minimum percentage of phosphorous in an amount of about 0.7%, in some aspects about 0.75%, and in some other aspects about 0.8%; a minimum amount of copper of about 3 ppm, in some aspects about 4 ppm, in some aspects about 5 ppm, in some aspects about 6 ppm, and a maximum amount of copper of about 10 ppm, in some aspects about 9 ppm, in some aspects about 8 ppm, in some aspects about 7 ppm, and in some other aspects about 6 ppm; and a minimum selenium in an amount below detection limits of about 2.25 ppm In some aspects, the distillers meal as described herein is used as a feed supplement or feed formula for ducks and/or geese, including starter, grower, finisher, breeder developer and/or breeder. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; and a minimum percentage of phosphorous in an amount of about 0.7%, in some aspects about 0.75%, and in some other aspects about 0.8%.

In some aspects, the distillers meal as described herein is used as a feed supplement or feed formula for fish, including trout, catfish and other species other than trout or catfish. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a maximum percentage of crude fiber in an amount of about 7%, in some aspects about 6%, and in some aspects about 5%; and a minimum percentage of phosphorous in an amount of about 0.7%, in some aspects about 0.75%, and in some other aspects about 0.8%.

In some aspects, the distillers meal as described herein is used as a feed supplement or feed formula for rabbit, including grower and/or breeder. The distillers meal may have a minimum percentage of crude protein in an amount of about 28%, in some aspects about 29%, in some aspects about 30%, in some aspects about 31%, in some aspects about 32%, in some aspects about 33%, in some aspects about 34%, and in some aspects about 35%; a minimum percentage of crude fat in an amount of about 0.25%, in some aspects about 0.5%, in some aspects about 1%, in some aspects about 2%, in some aspects about 3%, in some aspects about 4%, and in some aspects about 5%; a minimum percentage of crude fiber in an amount of about 7%, in some aspects about 6%, and in some aspects about 5%; a maximum percentage of crude fiber in an amount of about 7%, in some aspects about 6%, and in some aspects about 5%; a minimum percentage of calcium in an amount of about 0.06%, in some aspects about 0.07%, and in some aspects about 0.08%, and a maximum percentage of calcium in an amount of about 0.2%, in some aspects about 0.1%, in some aspects about 0.15%, in some aspects about 0.095%, and in some other aspects about 0.09%; and a minimum percentage of phosphorous in an amount of about 0.7%, in some aspects about 0.75%, and in some other aspects about 0.8%.

EXAMPLES

Example 1

Corn DDGS from a dry grind corn ethanol biorefinery were subjected to a hexane extraction process as described herein to achieve corn distillers meal having desired nutritional qualities. A selection of the nutritional properties of the corn distillers meal is provided in Table 1.

TABLE 1

Nutritional Properties of De-oiled Corn Grain DDGs

| 06S-05686<br>DDG DE-OILED PLANT TRIAL | As Received<br>Basis | 100% Dry<br>Matter Basis |
|---|---|---|
| Total Moisture, % | 4.00 | 0.000 |
| Total Dry Matter, % | 96.0 | 100 |
| Karl Fisher Moisture, % | 2.63 | |
| Crude Protein, Combustion, % | 32.0 | 33.3 |
| Crude Fat (Diethyl Ether Extract), % | 3.03 | 3.16 |
| Ash, % | 4.66 | 4.85 |
| Crude Fiber, Crucible Method, % | 7.06 | 7.35 |
| Acid Detergent Fiber, % | 11.5 | 12.0 |
| Neutral Detergent Fiber, % | 25.6 | 26.7 |
| Nitrogen Free Extract, % | 49.0 | 51.0 |
| Alanine - Total, % | 2.26 | 2.35 |
| Ammonia - Total, % | 0.700 | 0.729 |
| Arginine - Total, % | 1.24 | 1.29 |
| Aspartic Acid - Total, % | 2.36 | 2.46 |
| Glutamic Acid - Total, % | 5.13 | 5.34 |
| Glycine - Total, % | 1.17 | 1.22 |
| Histidine - Total, % | 0.704 | 0.733 |
| Isoleucine - Total, % | 0.838 | 0.873 |
| Leucine - Total, % | 3.57 | 3.72 |
| Lysine - Total, % | 0.735 | 0.766 |
| Phenylalanine - Total, % | 1.41 | 1.47 |
| Proline - Total, % | 2.50 | 2.60 |
| Serine - Total, % | 1.58 | 1.65 |
| Threonine - Total, % | 1.13 | 1.18 |
| Tyrosine - Total, % | 1.20 | 1.25 |
| Valine - Total, % | 1.21 | 1.26 |
| TDN (Proximate), % | 75.7 | 78.9 |
| NE/Lactation (Proximate), Mcal/lb | 0.79 | 0.82 |
| NE/Maintenance (Proximate), Mcal/lb | 0.83 | 0.86 |
| Metabolizable Energy, kcal/lb | 1180 | 1230 |
| NE/Gain (Proximate), Mcal/lb | 0.55 | 0.57 |

Example 2

Corn DDGS from a dry grind corn ethanol biorefinery were subjected to a hexane extraction process as described herein to achieve corn distillers meal having desired physical and nutritional properties. A selection of the physical and nutritional properties of the corn distillers meal are provided below in Table 3 and Table 4.

The corn distillers meal was then subjected to two different pelleting processes. The pelleting conditions are described below in Table 2, with "Run 1" representing the first pelleting process and "Run 2" representing the second pelleting process. A selection of the physical and nutritional properties of the pelleted corn distillers meal produced in the two pelleting runs are provided below in Table 3 and Table 4.

| Processing Conditions used for Pelleting Distillers Meal | | | | |
|---|---|---|---|---|
| | Run 1 | | Run2 | |
| | Mean | St Dev | Mean | St Dev |
| Pellet Mill | CPM#3016 | | CPM # 3016 | |
| Die Length/Die Diameter | 2.25"/3/16" | | 2.25"/3/16" | |
| Mill discharge temp (° F.) | 170.22 | 3.87 | 172.90 | 3.32 |
| System motor load (kW) | 39.39 | 7.81 | 29.82 | 1.91 |
| Throughput (tons/hr) | 1.91 | 0.39 | 1.13 | 0.04 |

TABLE 3

Physical Properties of Distillers Meal and Pelletized Distillers Meal

| | Meal | | Run 1 | | Run 2 | |
|---|---|---|---|---|---|---|
| Property | Mean | St Dev | Mean | St Dev | Mean | St Dev |
| Moisture content (%, wb) | 10.89 | 0.25 | 7.64 | 0.35 | 7.52 | 0.27 |
| Water activity (—) | 0.48 | 0.00 | 0.36 | 0.00 | 0.35 | 0.00 |
| Particle size - GMD (mm) | 0.65 | — | — | — | — | — |
| Particle size - GSD (mm) | 1.87 | — | — | — | — | — |
| Thermal - conductivity (W/mC) | 0.08 | 0.00 | — | — | — | — |
| Thermal - diffusivity (mm$^2$/s) | 0.12 | 0.00 | — | — | — | — |
| Color - L (—) | 45.10 | 0.99 | 35.45 | 0.49 | 34.62 | 0.84 |
| Color - a (—) | 9.00 | 0.21 | 7.05 | 0.42 | 7.03 | 0.28 |
| Color - b (—) | 19.37 | 0.40 | 14.05 | 0.63 | 13.74 | 0.46 |
| Fines (%) | — | — | 10.00 | 3.00 | 3.00 | 0.00 |
| Pellet Durability Index (%) | — | — | 61.97 | 1.82 | 71.98 | 2.22 |
| Bulk density (lb/ft$^3$) | 30.71 | 0.06 | 31.96 | 0.35 | 35.04 | 0.12 |
| Angle of repose (°) | 14.99 | 0.51 | 19.82 | 1.66 | 17.87 | 0.49 |
| Unit density (kg/m$^3$) | — | — | 727.17 | 97.21 | 605.70 | 98.64 |

TABLE 4

Nutritional Properties of Distillers Meal and Pelletized Distillers Meal

| | De-oiled | | Pellets | | | |
|---|---|---|---|---|---|---|
| | DDGS | | Run 1 | | Run 2 | |
| Moisture Content (%, wb) | 10.89 | 0.25 | 7.65 | 0.35 | 7.52 | 0.27 |
| Protein (%, db) | 34.35 | 0.07 | 34.15 | 0.07 | 33.50 | 0.14 |
| Fiber (%, db) | 8.20 | 0.14 | 8.20 | 0.28 | 8.00 | 0.28 |
| Fat (%, db) | 2.65 | 0.07 | 4.95 | 0.07 | 5.10 | 0.14 |
| Ash (%, db) | 5.01 | 0.03 | 4.97 | 0.09 | 4.98 | 0.01 |
| Nitrogen Free Extract (%, db) | 49.75 | 0.21 | 47.75 | 0.49 | 48.45 | 0.35 |

Example 3

In the following example, corn distillers meal as described herein was used as a feed supplement in finishing cattle diets. The performance of the diets supplemented with the corn distillers meal was compared to a control diet that did not utilized corn distillers meal as a feed supplement.

Three finishing cattle diets, including a control diet lacking corn distillers meal and two finishing cattle diets including a supplement of corn distillers meal, were designed for the study. Substitutions were iso-nitrogenous where corn distillers meal replaced corn, soy bean mean ("SBM") and urea. As shown in Table 5, the three diets all contained a fixed amount of a liquid supplement formulation including urea, monensin and tylosin, and other micro-ingredients at the same concentration for all three diets. The three diets were: 1) SBM/urea as a control diet typical for feed lots; 2) corn distillers meal replacing SBM and dry urea; and 3) corn distillers meal/SBM where corn distillers meal replaced 90% of the SBM and the dry urea.

TABLE 5

| | Diet 1 SBM | Diet 2 Corn Distillers Meal | Diet 3 10% SBM 90% Corn Distillers Meal |
|---|---|---|---|
| Grass Hay % | 4.04 | 4.05 | 4.05 |
| Whole shelled corn %[2] | 53.73 | 47.45 | 47.84 |
| High moisture ear corn % | 32.33 | 32.43 | 32.41 |
| Liquid supplement %[2] | 4.47 | 4.48 | 4.48 |

TABLE 5-continued

| | Diet 1 SBM | Diet 2 Corn Distillers Meal | Diet 3 10% SBM 90% Corn Distillers Meal |
|---|---|---|---|
| Pelleted supplement % | 5.44 | 11.59 | 11.23 |
| SBM[3] | (5.02) | — | (1.12) |
| Urea[3] | (0.42) | — | — |
| Corn distillers meal[3] | — | (11.59) | (10.11) |
| Dry matter (DM)% | 74.93 | 74.84 | 74.88 |
| Crude protein (CP)% | 13.28 | 13.20 | 13.24 |
| Neutral Detergent Fiber (NDF) %[a] | 14.43 | 18.40 | 17.93 |
| Ash %[a] | 2.50 | 2.68 | 2.67 |

[1]All values except dry matter (DM) on DM basis.
[2]Contained 45% CP from Urea; 678 g/T monesin; 164 g/T tylosin; fortified with minerals and vitamins to meet or exceed NRC requirements.
[3]Values in parentheses are totaled as Pelleted Supplement.
[4]Treatments differ (P < 0.01)

The cattle had been in the feedlot for more than 60 days prior to beginning the study. There were 48 steers randomly assigned to each of the three diets, 6 steers in 8 pens for each diet. The total number of steers was 144. Cattle were fed twice daily in equal proportions over the course of the 132 day study. All individual steer body weights were measured in the morning before feed was delivered. There was no fasting or water deprivation. Step-up diets were used to acclimatize the steers to the study diets and the final diets were first offered on day 22 of the study. On day 28 of the study, the steers were implanted with Revalor® S, available from Intervet Inc.

The data for average daily gain (ADG), dry matter intake (DMI), and pounds feed/average daily gain (F/G) were collected and compiled along with body weight and feed records. For all interim period reporting, performance calculations were made using unshrunk body weights. For cumulative performance calculations, final body weight (BW) was shrunk by 3%. The final live body weight of each of the study animals was calculated as hot carcass weight (HCW) divided by a constant dressing percentage of 62.5%. On day 132 of the feedlot study, only the morning feed was delivered and the cattle were harvested the following morning.

Results

The results of this study show that corn distillers meal can be used as a feed supplement and source of CP without any loss of carcass quality or steer health. More particularly, the study indicates that corn distillers meal may be used as a feed supplement for carbohydrates, protein, as well as non-protein nitrogen (NPN) containing compounds. As shown by Table 5, the corn distillers meal was used in Diet 2 and Diet 3 as a substitute for at least part of the CP from SBM, along with approximately 0.42% by weight of urea, and approximately 6.5% by weight of dietary corn, relative to the control diet.

Referring to Table 6, steers fed corn distillers meal had significantly higher (P<0.05) initial ADG at day 28 and day 56, when compared to steers fed the control diet. The corn distillers meal diet contained more neutral detergent fiber than the control diet and digesta retention time and water holding may therefore be increased. Diet 2 and Diet 3 had a marginally higher DMI, relative to the control diet. However, as shown in Table 6, the slightly higher DMI did not correspond to significant differences in ADG for the study.

With continued reference to Table 6, after day 112, the ADG was very similar for each of the diets at each of the testing intervals. Also, the F/G ratio of the de-oiled diets was comparable to the SBM/urea control diet—ranging from approximately 6.67-6.83 pounds on day 112 and from approximately 5.91-6.13 pounds on day 132.

Tables 7 and 8 show the cumulative data collected during the study and the carcass traits of the harvested steers. As shown in Table 6, the slightly higher DMI for the corn distillers meal substituted diets did not correspond to significant differences in diet ADG for the length of the study. The cumulative DMI was less than 3% greater for corn distillers meal in contrast to the SBM/urea control diet. As shown in the bottom half of Table 7, the carcass adjusted final body weight, as derived from the hot carcass weight (HCW), were very similar among the test diets. The final F/G ratio, carcass adjusted, was 5.83 lbs in the SBM/urea control diet. The F/G ratio in the corn distillers meal diets was 5.81 lbs and 5.76 lbs. The comparable F/G ratios indicate that the corn distillers meal substituted diets are just as effective as the control diet for inducing a steadily increasing body weight for the length of the study. Moreover, as shown in Table 5, the carcass traits of the corn distillers meal diet were similar to the carcass traits of the control diet.

TABLE 6

| | Treatment | | | |
|---|---|---|---|---|
| | Diet 1 SBM/urea | Diet 2 Corn Distillers Meal | Diet 3 SBM/Corn Distillers Meal | SEM |
| Initial BW lb | 769 | 769 | 771 | 2.0 |
| Day 28 BW lb | 887$^b$ | 891$^b$ | 903$^a$ | 2.7 |
| ADG lb | 4.21$^b$ | 4.38$^b$ | 4.71$^a$ | 0.087 |
| DMI lb | 17.15$^b$ | 17.47$^{ab}$ | 17.63$^a$ | 0.118 |
| F/G | 4.07$^b$ | 4.00$^b$ | 3.74$^a$ | 0.104 |
| Day 56 BW lb | 1022 | 1044 | 1033 | 6.1 |
| ADG lb | 4.82$^a$ | 5.44$^b$ | 4.65$^a$ | 0.195 |
| DMI lb | 22.17 | 23.17 | 22.70 | 0.393 |
| F/G | 4.62$^{ab}$ | 4.26$^a$ | 4.93$^b$ | 0.166 |
| Day 84 BW lb | 1137$^b$ | 1155$^a$ | 1147$^b$ | 4.6 |
| ADG lb | 4.12 | 3.98 | 4.07 | 0.132 |
| DMI lb | 24.02 | 24.55 | 24.11 | 0.273 |
| F/G | 5.84 | 6.19 | 5.97 | 0.224 |
| Day 112 BW lb | 1244$^a$ | 1264$^b$ | 1256$^a$ | 6.3 |
| ADG lb | 3.82 | 3.90 | 3.89 | 0.143 |
| DMI lb | 25.50$^a$ | 26.51$^b$ | 25.81$^a$ | 0.149 |
| F/G | 6.76 | 6.83 | 6.67 | 0.258 |
| Day 132 BW lb | 1331 | 13.50 | 1339 | 7.8 |
| ADG lb | 4.33 | 4.31 | 4.16 | 0.216 |
| DMI lb | 25.38 | 2576 | 25.39 | 0.420 |
| F/G | 5.91 | 6.10 | 6.13 | 0.236 |

$^{ab}$Means without common superscripts differ (P < 0.05)

TABLE 7

| | Treatment | | | |
|---|---|---|---|---|
| | Diet 1 SBM/urea | Diet 2 Corn Distillers Meal | Diet 3 SBM/Corn Distillers Meal | SEM |
| Final BW$^1$ lb | 1291 | 1310 | 1299 | 7.6 |
| ADG lb | 3.95 | 4.10 | 4.00 | 0.054 |
| DMI lb | 22.69 | 23.35 | 22.99 | 0.218 |
| F/G | 5.75 | 5.70 | 5.75 | 0.050 |
| | Carcass adjusted | | | |
| Final BW$^2$ | 1283 | 1298 | 1298 | 7.6 |
| ADG | 3.90 | 4.02 | 3.99 | 0.047 |
| F/G | 5.83 | 5.81 | 5.76 | 0.063 |

TABLE 8

| | Diet | | | |
|---|---|---|---|---|
| | Diet 1 SBM/urea | Diet 2 Corn Distillers Meal | Diet 3 SBM/Corn Distillers Meal | SEM |
| Dress %$^2$ | 62.1 | 62.0 | 62.5 | 0.26 |
| HCW lb | 802 | 812 | 812 | 4.1 |
| REA in.$^2$ | 12.49 | 12.69 | 12.87 | 0.182 |
| KPH % | 2.35 | 2.31 | 2.28 | 0.037 |
| Marbling Score$^3$ | 5.63 | 5.47 | 5.78 | 0.112 |
| Yield Grade | 3.33 | 3.30 | 3.40 | 0.069 |
| Choice & Prime % | 81.0 | 79.5 | 80.2 | 5.61 |

Example 4

In the following example, corn DDGS from a dry grind corn ethanol biorefinery were subjected to a hexane extraction process as described herein to achieve crude corn oil. More particularly, corn DDGS were obtained from the removal of ethyl alcohol by distillation from the yeast fermentation of corn by condensing and drying the solids of the resultant whole stillage by methods employed in the grain distilling industry using the dry milling process. The crude corn oil is further removed from the corn DDGS by hexane extraction for use as food grade corn oil or for the production of biodiesel and glycerine. A selection of the nutritional properties of the extracted crude corn oil are provided in Table 9.

TABLE 9

Oil Extracted From DDGS

| | As Received Basis | 100% Dry Matter Basis |
|---|---|---|
| Karl Fisher Moisture % | 1.40 | — |
| Crude Protein % | 0.560 | 0.56 |
| Total Nitrogen % | 0.0895 | 0.089 |
| Ash % | 0.0800 | 0.6 |
| Calcium % | 0.00800 | 0.008 |
| Cobolt, ug/g (ppm) | — | <0.1 |
| Copper, ug/g (ppm) | — | <2.0 |
| Iron, ug/g (ppm) | 14.9 | 14.9 |
| Magnesium % | 0.00500 | 0.005 |
| Molybdenum, ug/g (ppm) | — | <0.20 |
| Manganese, ug/g (ppm) | — | <1.0 |
| Phosphorus % | 0.0180 | 0.018 |
| Potassium % | 0.00600 | 0.006 |
| Sodium % | 0.00300 | 0.003 |
| Sulfur % | 0.0190 | 0.019 |
| Zinc, ug/g (ppm) | 2.40 | 2.40 |
| Free Fatty Acids as Oleic % | 9.9 | 9.9 |

Example 5

Corn DDGS from a dry grind corn ethanol biorefinery were subjected to a commercial grade hexane extraction process as described herein to achieve corn distillers meal having desired nutritional qualities. A selection of the nutritional properties of the original DDGS and the corn distillers meal are provided in Table 10.

TABLE 10

Nutritional Properties of Original DDGS and De-Oiled DDGS

| | Original DDGS | | De-Oiled DDGS | |
|---|---|---|---|---|
| | As Received Basis | 100% Dry Matter Basis | As Received Basis | 100% Dry Matter Basis |
| Total Moisture, % | 7.57 | 0.000 | 4.93 | 0.000 |
| Total Dry Matter, % | 92.4 | 100 | 95.1 | 100 |
| Karl Fisher Moisture, % | 5.80 | | 3.01 | |
| Crude Protein, Combustion, % | 27.3 | 29.5 | 31.3 | 32.9 |
| Crude Fat (Ether Extract), % | 11.6 | 12.6 | 2.53 | 2.66 |
| Ash, % | 4.29 | 4.64 | 4.91 | 5.16 |
| Crude Fiber, % | 6.49 | 7.02 | 6.23 | 6.55 |
| Acid Detergent Fiber, % | 9.70 | 10.5 | 12.0 | 12.6 |
| Neutral Detergent Fiber, % | 21.3 | 23.0 | 24.6 | 25.8 |
| Nitrogen Free Extract, % | 42.7 | 46.2 | 50.0 | 52.6 |
| Total Nitrogen, % | 4.37 | 4.73 | 5.01 | 5.27 |
| Calcium, % | 0.0750 | 0.0811 | 0.0940 | 0.0989 |
| Cobalt, ug/g (ppm) | | <0.1 | | <0.1 |
| Copper, ug/g (ppm) | 3.70 | 4.00 | 5.50 | 5.79 |
| Iron, ug/g (ppm) | 178 | 193 | 184 | 194 |
| Magnesium, % | 0.355 | 0.384 | 0.385 | 0.405 |
| Manganese, ug/g (ppm) | 18.2 | 19.7 | 23.3 | 24.5 |
| Molybdenum, ug/g (ppm) | 0.66 | 0.71 | 0.66 | 0.69 |
| Phosphorus, % | 0.759 | 0.821 | 0.852 | 0.896 |
| Potassium, % | 0.942 | 1.02 | 1.07 | 1.13 |
| Sodium, % | 0.320 | 0.346 | 0.361 | 0.380 |
| Sulfur, % | 0.772 | 0.835 | 0.865 | 0.910 |
| Zinc, ug/g (ppm) | 58.1 | 62.9 | 70.1 | 73.7 |
| TDN (Proximate), % | 79.1 | 85.6 | 74.9 | 78.8 |

As illustrated by the data provided in Table 10, in general the removal of oil from the corn DDGS such that the corn distillers meal contains a crude fat content less than about 5% increases the concentration of the other nutrients by approximately 10% for the de-oiled DDGS as compared to the original DDGS.

Example 6

Testing was done using standard Soxhlet apparatus and methodology for solvent extracting hexane soluble compounds DDGS. A control sample was initially run for the purpose of determining the total lipid content of the DDGS. In this trial, the standard AOCS method was used except that n-hexane was used as the solvent instead of the petroleum ether, which is called for in the AOCS method. Following determination of the total content of the lipids in the DDGS, additional trials were run where the standard AOCS method was further modified to more accurately represent full scale industrial conditions including, (a) the DDGS was extracted in their natural form (i.e., they were not fine ground into powder), and (b) the extraction time was reduced from 240 minutes to 60 minutes. Reference to "Coarse" in the results summarized Tables 11 and 12 refers to DDGS which was extracted in its natural form (unground). Reference to "Fine" in the results summarized in Tables 11 and 12 refers to DDGS which has been finely ground into powder form as called for in the AOCS method.

TABLE 11

Nutritional Properties of Original DDGS and De-Oiled DDGS

| | Course DDGS | | Fine DDGS | |
|---|---|---|---|---|
| | As Received | De-Oiled | As Received | De-Oiled |
| Total Moisture, % (m/m) | 11.5% | — | — | — |
| Crude Fat, (hexane extracted) % (m/m) | — | 7.79 | — | 9.83 |
| Crude Protein, as received % (m/m) | — | 31.87 | 29.75 | 31.14 |
| Crude Protein, dry matter % (m/m) | — | 36.01 | 33.62 | 35.19 |
| Phosphorus, as received % (m/m) | 0.604 | 0.620 | 0.594 | 0.625 |
| Phosphorus, dry matter % (m/m) | 0.682 | 0.700 | 0.671 | 0.706 |
| Potassium, as received % (m/m) | 0.910 | 0.879 | 0.874 | 0.873 |
| Potassium, dry matter % (m/m) | 1.028 | 0.994 | 0.988 | 0.986 |
| Calcium, as received % (m/m) | 0.024 | 0.026 | 0.023 | 0.026 |
| Calcium, dry matter % (m/m) | 0.027 | 0.029 | 0.026 | 0.029 |
| Magnesium, as received % (m/m) | 0.315 | 0.317 | 0.293 | 0.299 |
| Magnesium, dry matter % (m/m) | 0.356 | 0.358 | 0.331 | 0.338 |
| Zinc, as received (ppm) | 47.134 | 46.051 | 44.264 | 44.949 |
| Zinc, dry matter (ppm) | 53.259 | 52.035 | 50.016 | 50.790 |
| Manganese, as received (ppm) | 15.253 | 15.334 | 14.138 | 14.755 |
| Manganese, dry matter (ppm) | 17.235 | 17.327 | 15.975 | 16.672 |
| Copper, as received (ppm) | 4.037 | 4.469 | 4.124 | 4.307 |
| Copper, dry matter (ppm) | 4.561 | 5.050 | 4.660 | 4.866 |
| Iron, as received (ppm) | 81.254 | 88.923 | 95.229 | 80.817 |
| Iron, dry matter (ppm) | 91.812 | 100.478 | 107.603 | 91.319 |
| Sodium, as received % | 0.158 | 0.157 | 0.153 | 0.159 |
| Sodium, dry matter % | 0.179 | 0.177 | 0.173 | 0.180 |
| Sulfur, as received % | 0.491 | 0.526 | 0.485 | 0.520 |
| Sulfur, dry matter % | 0.555 | 0.594 | 0.548 | 0.587 |

With respect to the summarized data in Table 11, the components in the dry matter form are restated below with a concentration by hexane extraction being determined.

TABLE 12

Concentration Extraction - Resulting Percentages

| | Course DDGS | | Concentration |
|---|---|---|---|
| | As Received | De-Oiled | by Extraction |
| Crude Fat, (hexane extracted) % (m/m) | — | 7.79 | 108% |
| Phosphorus, dry matter % (m/m) | 0.682 | 0.700 | 103% |
| Potassium, dry matter % (m/m) | 1.028 | 0.994 | 97% |
| Calcium, dry matter % (m/m) | 0.027 | 0.029 | 107% |
| Magnesium, dry matter % (m/m) | 0.356 | 0.358 | 101% |
| Zinc, dry matter (ppm) | 53.259 | 52.035 | 98% |
| Manganese, dry matter (ppm) | 17.235 | 17.327 | 101% |
| Copper, dry matter (ppm) | 4.561 | 5.050 | 111% |
| Iron, dry matter (ppm) | 91.812 | 100.478 | 109% |
| Sodium, dry matter % | 0.179 | 0.177 | 99% |
| Sulfur, dry matter % | 0.555 | 0.594 | 107% |

For the data in Table 12, a concentration factor was calculated, which represents the amount of (lipid) mass removed from the DDGS sample by hexane extraction. By removing oil using a hexane solvent extraction, it is expected that the remaining non-hexane soluble compounds should be concentrated by approximately 108%. Therefore, if the metal or trace mineral in the DDGS sample is non-soluble in hexane, the concentration in DDGS should go up by approximately 108% after extraction. As provided in the data summarized in Table 12, the concentration in DDGS went up to about 108% for calcium, iron, copper and sulfur, which indicates that the foregoing compounds are not extracted within the hexane during hexane solvent extraction of the DDGS.

However if the metal or trace mineral is hexane soluble (i.e., in the form of a hexane soluble compound or complex), then the ratio should not change and the concentration factor should remain close to approximately 100%. As provided in the data summarized in Table 12, the concentration DDGS remained about 100% for potassium, magnesium, manganese, zinc and sodium, which indicates that the foregoing compounds are extracted within the hexane during hexane solvent extraction of the DDGS.

As indicated in the data summarized in Table 12 for phosphorous, the concentration factor for phosphorous did not remain about 100% nor did it increase to about 108%; instead, the concentration was about 103%. Without wishing to be bound by theory, there may be two or more forms of phosphorous in DDGS, with one or more inorganic compound(s) or complex(es) containing phosphorus and the other being phospholipids, which are known to be soluble in hexane and therefore extracted (i.e., the 100% concentration factor). This implies that the remaining phosphorous compound(s) or complex(s) in DDGS must be inorganic compound(s) or complex(es) containing phosphorous (i.e., the 108% concentration factor). Thus, at least a portion of the phosphorous and/or phosphorous containing compound(s) or complex(s) are extracted within the hexane during hexane solvent extraction of the DDGS.

Since only a portion of the phosphorous and/or phosphorous containing compound(s) or complex(s) are extracted within the hexane during hexane solvent extraction of the DDGS, the extracted oil with a reduced phosphorous content may be used in the hydrotreating process to produce a diesel fuel without necessarily requiring additional treatment of the extracted oil to address the phosphorous content.

Example 7

Testing was done on the oil extraction of DDGS relating to coarse DDGS and fine DDGS. In this trial, oil in the DDGS was solvent extracted using commercial grade hexane. Samples of the coarse DDGS and fine DDGS were analyzed at intervals of 15 minutes, 30 minutes, 60 minutes, and 90 minutes. Reference to "Coarse" in the results summarized in Table 13 refers to DDGS which was extracted in its natural form (unground), which particle size distribution by weight and size are provided in Tables 14 and 15. Reference to "Fine" in the results summarized in Table 13 refers to DDGS that finely ground into powder form and all passed thru a 1 mm screen as called for in the AOCS Soxhlet method, which particle size distribution by weight and size are provided in Tables 14 and 15. The oil content of the coarse DDGS sample had a starting oil content of about 9.53% while the fine DDGS had a starting oil content of about 10.65% by weight.

TABLE 13

DDGS Particle Size on Oil Extraction

| Time, min. | Coarse DDGS | | Fine DDGS | |
|---|---|---|---|---|
| | % oil extracted | % residual oil | % oil extracted | % residual oil |
| 0 | — | 9.53 | — | 10.65 |
| 15 | 66.3 | 3.59 | 94.8 | 0.56 |
| 30 | 68.8 | 3.32 | 95.0 | 0.53 |
| 60 | 72.9 | 2.89 | 95.7 | 0.46 |
| 90 | 70.5 | 3.14 | 96.3 | 0.39 |

TABLE 14

DDGS Particle Size - Weight Percentage

| U.S. Sieve No. | Coarse DDGS (% Retained) | Fine DDGS (% Retained) |
|---|---|---|
| 6 | 0.2 | 0.0 |
| 8 | 0.4 | 0.0 |
| 12 | 1.2 | 0.0 |
| 16 | 11.5 | 0.0 |
| 20 | 26.6 | 0.0 |
| 30 | 51.4 | 13.1 |
| 40 | 45.0 | 14.7 |
| 50 | 7.6 | 0.4 |
| 70 | 15.1 | 2.5 |
| 100 | 5.1 | 1.0 |
| 140 | 2.1 | 0.1 |
| 200 | 0.3 | 0.0 |
| 270 | 0.0 | 0.0 |
| Pan | 0.0 | 0.0 |
| Average Particle Size (microns) | 591.20 | 521.35 |

TABLE 15

DDGS Particle Size - Quantity Percentage

| U.S. Sieve No. | Coarse DDGS (% Retained) | Fine DDGS (% Retained) |
|---|---|---|
| 6 | 0.13 | 0.0 |
| 8 | 0.22 | 0.0 |
| 12 | 0.73 | 0.0 |
| 16 | 6.90 | 0.0 |
| 20 | 16.02 | 0.13 |
| 30 | 30.88 | 41.24 |
| 40 | 27.02 | 26.26 |

TABLE 15-continued

| | DDGS Particle Size - Quantity Percentage | |
|---|---|---|
| U.S. Sieve No. | Coarse DDGS (% Retained) | Fine DDGS (% Retained) |
| 50 | 4.58 | 1.20 |
| 70 | 9.06 | 7.95 |
| 100 | 3.05 | 3.03 |
| 140 | 1.26 | 0.19 |
| 200 | 0.16 | 0.0 |
| 270 | 0.0 | 0.0 |
| Pan | 0.0 | 0.0 |
| TOTAL | 100 | 100 |
| Average Particle Size (microns) | 591.20 | 521.35 |

As provided in the data summarized in Table 13, coarse DDGS that is provided in its natural form (i.e., unground), resulted in a residual oil content of about 3% after 90 minutes. In contrast, the DDGS that was all ground to a particle size less than about 1 mm resulted in a residual oil content of about 0.39% after 90 minutes. Similarly, the percentage of oil extracted from DDGS using solvent extraction increased as the particle size of the DDGS was reduced.

It should be emphasized that the described embodiments of this disclosure are merely possible examples of implementations and are set forth for a clear understanding of the principles of this disclosure. Many variations and modifications may be made to the described embodiments of this disclosure without departing substantially from the spirit and principles of this disclosure. All such modifications and variations are intended to be included herein within the scope of this disclosure and protected by the following claims.

The invention claimed is:

1. Distillers meal comprising: a crude protein content ranging from about 28% to about 35% by weight on a dry matter basis, a crude fat content ranging from about 0.25% to about 6% by weight on a dry matter basis, and a residual level of a non-polar solvent in an amount of about 10 ppm to about 1000 ppm.

2. The distillers meal of claim 1, further comprising an initial sulfur and sulfur containing compounds in an amount of at least 0.5% by weight on a dry matter basis.

3. The distillers meal of claim 2, further comprising a neutral detergent fiber content ranging from about 25% to about 35% by weight and an acid detergent fiber content ranging from about 11.5% to about 16.5%.

4. The distillers meal of claim 1, further comprising a content of phosphorous and phosphorous containing compounds in amount of at least 0.8% by weight on a dry matter basis.

5. The distillers meal of claim 1, wherein the distillers meal comprises a residual level of the non-polar solvent in an amount of about 10 ppm to about 500 ppm.

6. The distillers meal of claim 5, wherein the distillers meal is corn distillers meal produced by solvent extraction of corn distillers dried grains with solubles.

7. The distillers meal of claim 5, wherein the distillers meal is produced by solvent extraction of corn distillers dried grains with soluble, the solvent comprising the non-polar solvent having a boiling point in the range of about 36° C. to about 99° C.

8. The distillers meal of claim 7, wherein the non-polar solvent comprises one or more alkanes $C_5$-$C_7$-alkanes chosen from n-pentane, n-hexane, n-heptane, isopentane, neopentane, isohexane, 2-methylepentane, 2,3-dimethylbutane, neohexane, isoheptane, 2-methylhexane, 2,2-dimethylpentane, 2,3-dimethylpentane, 2,4-dimethyl pentane, 3-ethylpentane, and 2,2,3-trimethylbutane, petroleum ether, or mixtures thereof.

9. The distillers meal of claim 1, further comprising a lysine content in an amount of about 0.7% to about 1.0%.

10. The distillers meal of claim 9, wherein a ratio of lysine content to a residual fat content is greater than about 20 and up to about 400.

11. The distillers meal of claim 1, further comprising a ratio of a total nitrogen content to a total free fatty acids content in an amount greater than about 25 up to about 200.

12. The distillers meal of claim 1 provided in an animal feed or an animal feed supplement for beef cattle, dairy cattle, equine, sheep, swine, fish, chickens, geese, turkey, rabbits or goats.

13. The distillers meal of claim 1, wherein the distillers meal is substantially free of a non-native emulsifier or a non-native flocculent.

14. The distillers meal of claim 1, wherein the distillers meal has at least a 50% reduced level of an emulsifier or a flocculent than distillers dried grain solubles that has been subjected to a corn stillage oil recovery process.

15. The distillers meal of claim 1, wherein at least 95% of the distillers meal has a particle size less than about 1 millimeter.

16. An animal feed ingredient comprising: corn distillers meal having a crude protein content ranging from about 28% to about 35% by weight, a crude fat content ranging from about 0.25% to about 6% by weight, a content of phosphorous and phosphorous containing compounds in an amount of at least 0.8% by weight, and a residual level of a non-polar solvent in an amount of about 10 ppm to about 1000 ppm.

17. The animal feed ingredient of claim 16, wherein the corn distillers meal is a feed supplement in an amount ranging from about 5% to about 75% by weight of the total feed on a dry matter basis.

18. The animal feed ingredient of claim 16, wherein the corn distillers meal is a feed supplement or a formula feed one or more animals chosen from beef cattle, dairy cattle, equine, swine, chickens, turkeys, goat, sheep, ducks, geese, fish, or rabbits.

19. The animal feed ingredient of claim 16, wherein the corn distillers meal has a potassium content of at least 0.8% by weight.

20. The animal feed ingredient of claim 16, wherein the crude fat content ranging from about 0.5% to about 3% by weight.

21. The animal feed ingredient of claim 20, wherein the crude protein content ranging from about 30% to about 35% by weight.

22. The animal feed ingredient of claim 16, wherein at least 95% of the corn distillers meal has a particle size less than about 1 millimeter.

23. The animal feed ingredient of claim 16, wherein the corn distillers meal is produced by solvent extraction of corn distillers dried grains with soluble, the solvent comprising the non-polar solvent having a boiling point in the range of about 36° C. to about 99° C.

24. The animal feed ingredient of claim 16, wherein the non-polar solvent comprises one or more alkanes $C_5$-$C_7$-alkanes chosen from n-pentane, n-hexane, n-heptane, isopentane, neopentane, isohexane, 2-methylepentane, 2,3-dimethylbutane, neohexane, isoheptane, 2-methylhexane, 2,2-dimethyl pentane, 2,3-dimethylpentane, 2,4-dimethylpentane, 3-ethylpentane, and 2,2,3-trimethylbutane, petroleum ether, or mixtures thereof.

25. The animal feed ingredient of claim 16, wherein the corn distillers meal further comprising a lysine content in an amount of about 0.7% to about 1.0%.

26. The animal feed ingredient of claim 25, wherein a ratio of lysine content to a residual fat content is greater than about 20 and up to about 400.

27. The animal feed ingredient of claim 16, wherein the corn distillers meal further comprising a ratio of a total nitrogen content to a total free fatty acids content in an amount greater than about 25 up to about 200.

28. The animal feed ingredient of claim 16 provided for beef cattle, dairy cattle, equine, sheep, swine, fish, chickens, geese, turkey, rabbits or goats.

29. The animal feed ingredient of claim 16, wherein the corn distillers meal is substantially free of a non-native emulsifier or a non-native flocculent.

30. The animal feed ingredient of claim 16, wherein the corn distillers meal has at least a 50% reduced level of an emulsifier or a flocculent than distillers dried grain solubles that has been subjected to a corn stillage oil recovery process.

31. The animal feed ingredient of claim 30, wherein at least 95% of the corn distillers meal has a particle size less than about 1 millimeter.

32. The animal feed ingredient of claim 16, wherein at least the corn distillers meal is provided in the form of a pellet.

33. The animal feed ingredient of claim 16, wherein the corn distillers meal is a feed supplement in an amount ranging from about 50% to about 75% by weight of the total feed on a dry matter basis.

34. The distillers meal of claim 1 provided in the form of a pellet.

* * * * *